US012708532B2

(12) United States Patent
Gao et al.

(10) Patent No.: US 12,708,532 B2
(45) Date of Patent: Aug. 18, 2026

(54) CLOSED-LOOP FLUIDIC REGENERATIVE SYSTEM AND ACTIVE COMPRESSION BAND, APPAREL, DEVICE, FOOTWEAR AND METHOD

(71) Applicants: Run Ze Gao, Kitchener (CA); Carolyn Liqing Ren, Ontario (CA); Vivian Ngoc Tram Mai, Ontario (CA); Monica Roshni Maly, Ontario (CA); Kendal Ashton Marriott, Ontario (CA); James Yungjen Tung, Ontario (CA); Clark Rutherford Dickerson, Ontario (CA); Amanda Ann Patricia Johnson, Ontario (CA)

(72) Inventors: Run Ze Gao, Kitchener (CA); Carolyn Liqing Ren, Ontario (CA); Vivian Ngoc Tram Mai, Ontario (CA); Monica Roshni Maly, Ontario (CA); Kendal Ashton Marriott, Ontario (CA); James Yungjen Tung, Ontario (CA); Clark Rutherford Dickerson, Ontario (CA); Amanda Ann Patricia Johnson, Ontario (CA)

( * ) Notice: Subject to any disclaimer, the term of this patent is extended or adjusted under 35 U.S.C. 154(b) by 0 days.

(21) Appl. No.: 19/162,888

(22) PCT Filed: Feb. 29, 2024

(86) PCT No.: PCT/CA2024/050253
§ 371 (c)(1),
(2) Date: Sep. 5, 2025

(87) PCT Pub. No.: WO2024/182884
PCT Pub. Date: Sep. 12, 2024

(65) Prior Publication Data

US 2026/0115020 A1 Apr. 30, 2026

Related U.S. Application Data

(60) Provisional application No. 63/450,660, filed on Mar. 7, 2023.

(51) Int. Cl.
*A61F 2/74* (2006.01)
*A61F 2/66* (2006.01)
(Continued)

(52) U.S. Cl.
CPC ................ *A61F 2/74* (2021.08); *A61H 3/00* (2013.01); *A61F 2002/6614* (2013.01);
(Continued)

(58) Field of Classification Search
CPC ................ A61F 2/74; A61F 2002/6614; A61F 2002/6827; A61H 3/00; A61H 1/024;
(Continued)

(56) References Cited

U.S. PATENT DOCUMENTS

| | | | |
|---|---|---|---|
| 2,080,469 | A | 5/1937 | Gilbert |
| 5,558,627 | A | 9/1996 | Singer et al. |

(Continued)

FOREIGN PATENT DOCUMENTS

| | | |
|---|---|---|
| WO | 2020/216876 | 10/2020 |
| WO | 2020/257925 | 12/2020 |
| WO | 2021/149908 | 7/2021 |

OTHER PUBLICATIONS

International Search Report for PCT/CA2024/050253 (3 pages).
(Continued)

*Primary Examiner* — Tarla R Patel
(74) *Attorney, Agent, or Firm* — Barnes & Thornburg

(57) ABSTRACT

Disclosed herein are wearable devices for use with closed-loop fluidic regenerative systems comprising closed-loop fluidic regeneration module, fluidic transducers module, and fluidic transportation module. The system uses human gait
(Continued)

combined with closed-loop fluidic regenerative module to enable actuation of fluidic actuators to apply assistive, rehabilitative and/or therapeutic force, compression and/or torque to the human body. Human gait can also enable fluid sensors combined with a close-loop fluidic regenerative module to detect motion, characteristics, and/or positions of anatomical parts of the human body. In addition, disclosed herein are wearable active compression bands enabled by fluidic actuators that can apply smooth sequential gradient compression with cooling/icing effect in a wearable/portable profile. Closed-loop fluidic regenerative system combined with active compression band can achieve electronics-free active compression.

28 Claims, 15 Drawing Sheets

(51) Int. Cl.
*A61F 2/68* (2006.01)
*A61H 1/02* (2006.01)
*A61H 3/00* (2006.01)

(52) U.S. Cl.
CPC ...... *A61F 2002/6827* (2013.01); *A61H 1/024* (2013.01); *A61H 1/0266* (2013.01); *A61H 2201/1238* (2013.01); *A61H 2201/165* (2013.01)

(58) Field of Classification Search
CPC .......... A61H 1/0266; A61H 2201/1238; A61H 2201/165; A61H 1/0237; A61H 1/02; A61H 1/00; A61H 2001/027
See application file for complete search history.

(56) References Cited

U.S. PATENT DOCUMENTS

| | | | | |
|---|---|---|---|---|
| 5,713,141 | A | 2/1998 | Mitchell et al. | |
| 7,896,019 | B2 | 3/2011 | Bettin et al. | |
| 9,259,179 | B2 | 2/2016 | Stein | |
| 9,480,618 | B2 | 11/2016 | Hsiao-Wecksler et al. | |
| 10,744,021 | B1 | 8/2020 | Nace | |
| 2015/0209214 | A1* | 7/2015 | Herr | A61H 1/0266 623/27 |
| 2015/0305436 | A1 | 10/2015 | Doyle | |
| 2016/0278948 | A1* | 9/2016 | Piercy | A43B 7/20 |

OTHER PUBLICATIONS

Written Opinion for PCT/CA2024/050253 dated May 9, 2024 (3 pages).
"A wearable textile-based pneumatic energy harvesting system for assistive robotics" (https://doi.org/10.1126/sciadv.abo2418) by Shveda et al. (accessed Feb. 13, 2026, dated Aug. 24, 2022.
"A pneumatic power harvesting ankle-foot orthosis to prevent foot-drop" (https://doi.org/10.1186/1743-0003-6-19) by Chin et al., accessed Feb. 13, 2026, dated Jun. 16, 2009.

* cited by examiner

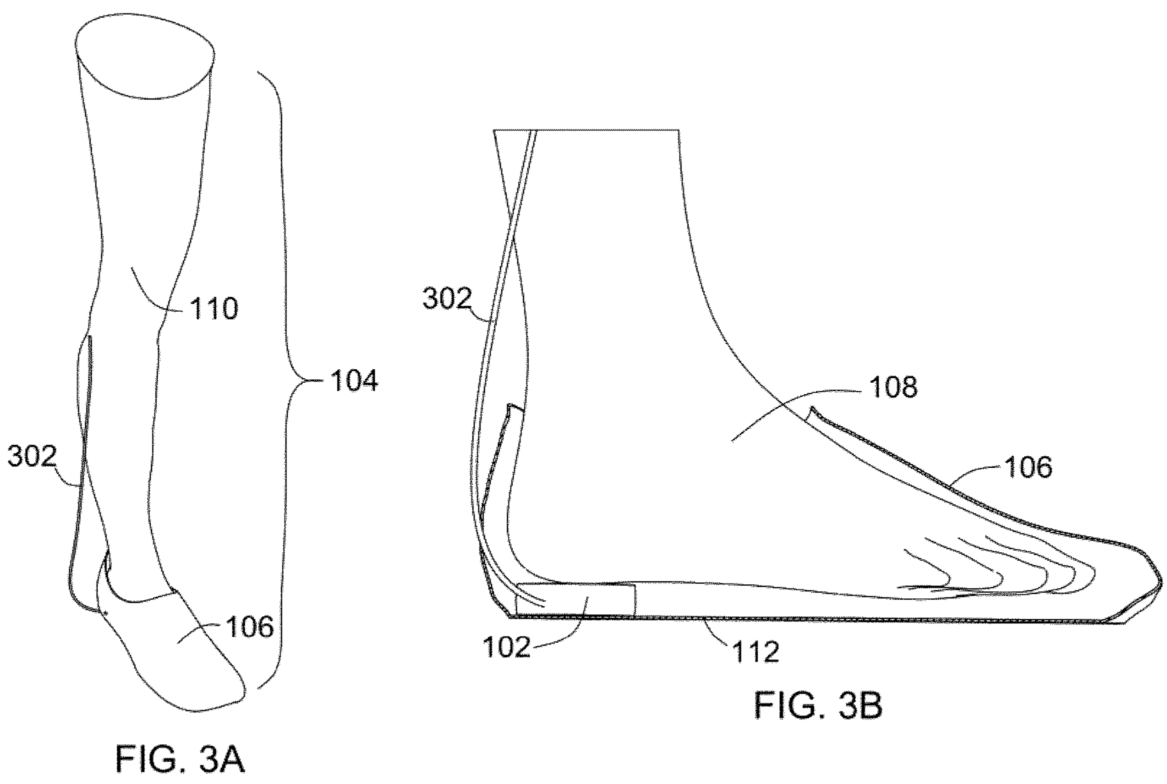
FIG. 3A
FIG. 3B
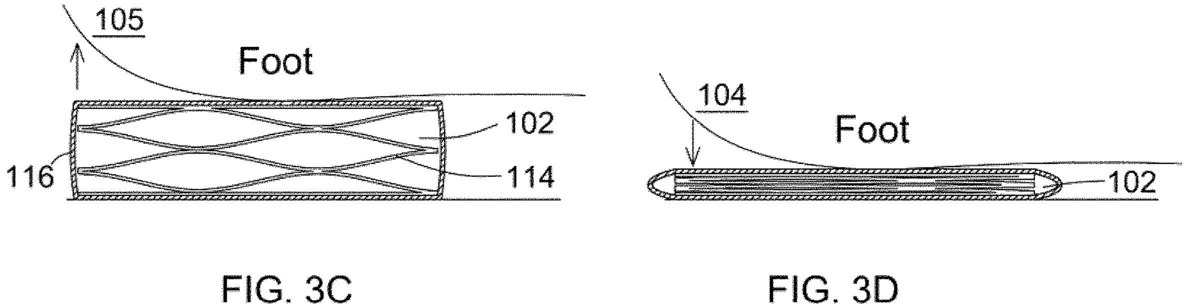
FIG. 3C
FIG. 3D 402
407
202
404
204
405
409
302
106

402
407
404
202
405
409
110
302
108
106
102

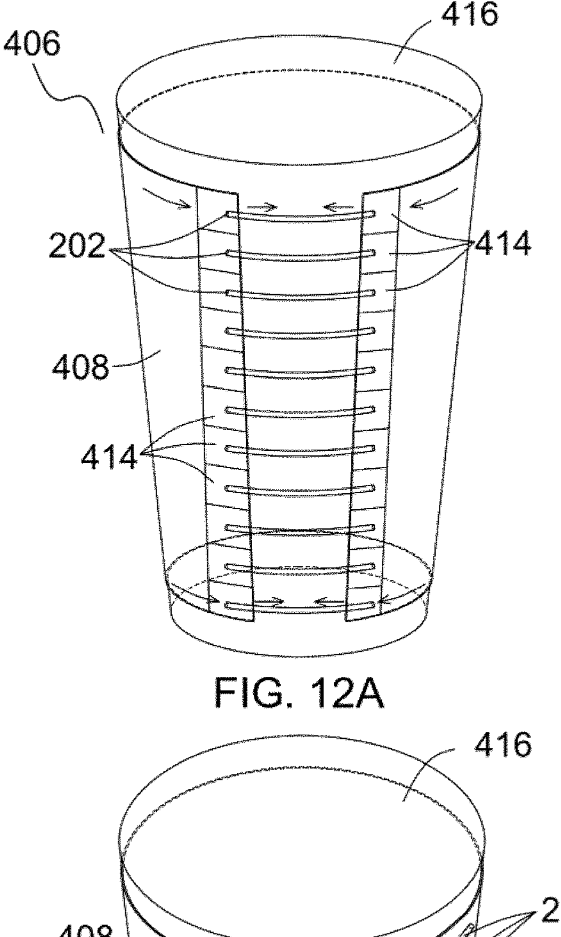
FIG. 12A
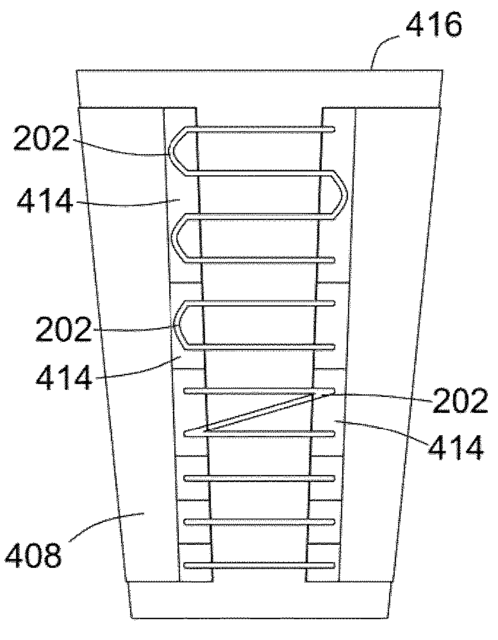
FIG. 12B
416
408
202
FIG. 12C

CLOSED-LOOP FLUIDIC REGENERATIVE SYSTEM AND ACTIVE COMPRESSION BAND, APPAREL, DEVICE, FOOTWEAR AND METHOD

CROSS-REFERENCE TO RELATED APPLICATIONS

This application is a United States nationalization under Section 371 of PCT Application No. PCT/CA2024/050253, filed on Feb. 29, 2024, which claims priority from U.S. Provisional Application No. 63/450,660, filed on Mar. 7, 2023, the entirety of each are hereby incorporated by reference herein.

FIELD OF THE INVENTION

The present invention generally relates to the field of assistive devices, and more specifically, to wearable dynamic assistive devices.

BACKGROUND OF THE INVENTION

Wearable assistive devices can often be divided into two categories: passive and active. Passive wearable assistive devices are generally mechanical without the requirement of electrical energy; thus, they are without a battery; however, their functionality is often limited as they are passive in nature, meaning that they may only provide a constant force, torque or a predetermined force or torque based on body motion or movement (i.e., body-driven systems). In the case of passive wearable sensors, they are also mechanical in nature without the need for a battery.

Active wearable assistive devices generally have actuators and/or sensors powered by electricity; thus they require a battery to operate. In most cases, active systems provide varied assistance based on control algorithms through sensor feedback. A major advantage of an active wearable assistive device is its ability to provide dynamic assistance. A major disadvantage commonly cited by end-user is the need for a battery that requires charging and a control box that is often bulky and cumbersome to wear.

Conventional compression systems, when combined with cooling/icing, normally require pumping and/or circulating cold water through one or a plurality of large hydraulic bladders surrounding a limb or a body part which makes the active compression sleeve and its control system bulky and heavy, thus making a wearable or portable system difficult to achieve.

Patent reference U.S. Pat. No. 5,713,141 may disclose cushioning devices for footwear with improved flexible barrier membranes that can be permanently inflated with gases such as nitrogen or air. The cushioning devices maintain the internal inflatant pressure for extended periods of time by employing a phenomenon referred to as diffusion pumping.

Patent reference U.S. Pat. No. 9,480,618 B2 may disclose a portable active fluid-powered ankle foot orthosis. A fluid-powered rotary actuator is configured to receive power from a wearable fluid power source and provide controlled force and resistance to aid or inhibit relative rotation of the foot bed and the lower leg mount.

Patent reference WO 2021/149908 A1 may disclose a knee brace for changing a contact pressure with respect to the body by using pneumatic pressure, wherein the knee brace generates a strong contact force in the stance phase and reduces the contact force in the swing phase.

Patent reference U.S. Pat. No. 10,744,021 B1 may disclose a knee brace that includes adjustable air bladders to absorb external forces before the external forces pass into the knee and cause internal knee injury, wherein a pair of struts are bifurcated by hinges, and the adjustable air bladders placed between the knee and the hinges.

Patent reference U.S. Pat. No. 5,558,627 may disclose an orthopedic brace for a joint includes a support mechanism attached to limb members on either side and an inflation mechanism operatively connected to an air bag and the sensors inflate the air bag in response to the trigger signal, thereby providing additional support to the joint before the joint is injured.

Patent reference U.S. Pat. No. 2015/0305436 A1 may disclose a pneumatically cushioned shoe or shoe insert device including a plastic layer forming air bladders. The air bladders pre-filled with air during manufacturing or filled with air by a user.

Patent reference U.S. Pat. No. 2,080,469 may disclose a pneumatic or inflatable foot correction appliance depending upon imprisoned air for the proper pressure application to the plantar or other regions of a foot.

Patent reference U.S. Pat. No. 9,259,179 B2 may disclose an orthopedic implant having an energy-harvesting device as a prosthetic component of a joint of the muscular-skeletal system.

Research journal article titled "A wearable textile-based pneumatic energy harvesting system for assistive robotics" (https://doi.org/10.1126/sciadv.abo2418) by Shveda et al. may disclose a textile-based pneumatic energy harvesting system for soft assistive robotics, where valves and energy storage components are used for creating motion and torque via soft robotic actuators for upper extremity applications.

Research journal article titled "A pneumatic power harvesting ankle-foot orthosis to prevent foot-drop" (https://doi.org/10.1186/1743-0003-6-19) by Chin et al. may disclose a pneumatic power harvesting ankle-foot orthosis to manage foot-drop. Ankle motion control is accomplished through a cam-follower locking mechanism actuated via a pneumatic circuit connected to the bellow pump and embedded in the foam sole.

However, the prior art canvassed above may have suffered from one or more significant problems and/or shortcomings. For example, all of this prior art may have suffered from one or more problems, including but not limited to the following: (a) lack of wearability regarding on-the-go usage; (b) inefficient and/or bulky actuation hardware; (c) unable to achieve sequential actuation; (d) unable to achieve actuation of fluidic actuators during stance phase of gait; (e) not designed for the applications described herein; (f) slow response time; (g) unable to be used as a sensing system; (h) poor user compliance, perhaps at least in part due to mechanical shortcoming and/or (i) challenging to manufacture.

It is an object of the present disclosure to obviate or mitigate one or more disadvantages and/or shortcomings associated with the prior art, and/or to meet or provide for one or more needs and/or advantages, and/or to achieve one or more objects of the present disclosure—one or more of which may preferably be readily appreciable by and/or suggested to those skilled in the art in view of the teachings and/or disclosures hereof.

BRIEF SUMMARY OF THE INVENTION

A wearable dynamic assistive device as disclosed herein uses closed-loop fluidic regeneration and/or an active compression band. The device uses one or a plurality of closed-loop fluidic regenerative devices to enable one or a plurality of fluidic transducers, including fluidic actuators or fluidic sensors, to achieve a variety of motion, movement, torques, and/or forces, achieving assistive, rehabilitative and/or therapeutic effect. In certain embodiments, active compression bands and fluidic actuators enable smooth-gradient compression with the possibility of cooling/icing simultaneously.

A wearable dynamic assistive device as described herein combines the best of both passive and active assistive devices based on the closed-loop fluidic regenerative system when combined with human gait. Most embodiments described herein are mechanical, specifically pneumatic or hydraulic; however, they are actively controlled by human gait. In other words, there are no batteries or electronics, but they are synchronized to dynamically tailor assistance or sensing based on the user's walking pattern and the user's weight when applied to the fluidic regenerative chamber. In turn, the fluidic energy generated by the fluidic regenerative chamber is transferred to fluidic actuators or sensors to apply augmenting forces, torques and/or motions to one or more anatomical parts of the human body and/or sense changes in the positions, compositions, states and/or locations of one or more anatomical part of the human body.

As noted above, conventional compression systems, when combined with cooling/icing, normally require pumping and/or circulating cold water through one or a plurality of large hydraulic bladders surrounding a limb or a body part which makes the active compression sleeve and its control system bulky and heavy, thus making a wearable or portable system difficult to achieve. To solve this problem, active compression sleeves with one or a plurality of active compression bands actuated by fluidic actuators can be used with active or passive cooling pads to achieve a wearable/portable compression and cooling/icing system while retaining the benefit of sequential gradient compression and/or articulations at joints.

There is disclosed herein a closed-loop fluidic regenerative (CLFR) device for use with one or more fluidic actuators and/or sensors to apply augmenting forces, torques and/or motions to one or more anatomical parts of the human body and/or sense changes in the positions, compositions, states and/or locations of one or more anatomical part of the human body. The device may comprise one or more closed-loop fluidic regeneration modules, one or more fluidic transportation modules, and/or one or more fluidic transducers modules. The closed-loop fluidic regenerative module preferably comprises at least one fluidic regeneration chamber, any number of energy supply mechanisms, and/or any number of energy return mechanisms. The fluidic transducers module may comprise any number of the following components: one or more fluidic transducers, such as one or more fluidic actuators or fluidic sensors, energy return mechanism, and/or pressure relief mechanism. The fluidic transportation module may comprise any number of the following components: fluidic conduits, fluidic valves, fluidic intake mechanism and fluidic filters. When the closed-loop fluidic regenerative module is actuated by compression or squeezing due to body weight during gait, particularly during the stance phase of gait, fluidic pressure and/or volume may be pushed into one or a plurality of fluidic transducers through fluidic transportation module. During the swing phase of gait, fluidic pressure and/or volume may return to at least one closed-loop fluidic regeneration module from one or a plurality of fluidic transducers. The advantages lie in not using any electronics and/or electrically-driven systems to actuate the fluidic transducers.

There is disclosed herein an active compression sleeve with one or a plurality of compression bands activated by one or a plurality of fluidic actuators. A single band may be activated by one or a plurality of fluidic actuators. When the fluidic actuator is activated (i.e., pressurized, depressurized, and/or vacuumed), the compression bands may tighten around a portion of the human body.

According to an aspect of some embodiments, fluidic intake mechanisms may, but need not necessarily, push fluid from the external atmosphere and/or environment into the internal closed-loop fluidic regenerative system.

According to an aspect of some embodiments, fluid may, but not necessarily, flow between any number of fluidic filters, fluidic valves, fluidic distribution mechanisms, fluidic regeneration chambers, fluidic actuators, and/or fluidic sensors.

According to an aspect of some embodiments, fluid may, but not necessarily, be released from the internal closed-loop fluidic regeneration systems through any number of pressure relief mechanisms manually and/or automatically.

According to an aspect of some embodiments, closed-loop fluidic regenerative modules may have one or a plurality of fluidic regeneration chambers.

According to an aspect of some embodiments, one or a plurality of fluidic regeneration chambers may, but need not necessarily, be located anywhere on the human body as long as it can be squeezed and/or compressed by a part of the human body with any other surface that is external or part of the human body during gait or any motion. The part of the human body may be one or a plurality of prostheses.

According to an aspect of a preferred embodiment, one or a plurality of fluidic regeneration chambers may, but need not necessarily, be placed at any location underneath the foot.

According to an aspect of some embodiments, one or a plurality of fluidic regeneration chambers may, but need not necessarily, be located between the bottom of the foot and the inside bottom surface of the footwear.

According to an aspect of some embodiments, one or a plurality of fluidic regeneration chambers may but need not necessarily, have any shape and/or size and may be placed at any location underneath the foot.

According to an aspect of some embodiments, one or a plurality of fluidic regeneration chambers may, but need not necessarily, be placed between the residual limb and the prosthetic socket with and/or without any liners and/or socks worn over the residual limb.

According to an aspect of some embodiments, one or a plurality of energy supply mechanisms may, but need not necessarily, be part of at least one fluidic regeneration chamber to displace fluid within at least one closed-loop fluidic regeneration module to another part of the internal system.

According to an aspect of some embodiments, one or a plurality of energy return mechanisms may, but need not necessarily, be part of at least one fluidic regeneration chamber to move fluidic pressure and/or volume from another part of the internal system to at least one fluidic regeneration chamber.

According to an aspect of some embodiments, one or a plurality of fluidic regeneration chambers may, but need not necessarily, be squeezed and/or compressed during the stance phase of gait.

According to an aspect of some embodiments, the squeeze or compression on one or a plurality of fluidic regeneration chambers may, but need not necessarily, be released completely or partially during the swing phase of gait.

According to an aspect of an embodiment, one or a plurality of fluidic regenerative chambers may, but need not necessarily, be placed from the medial of the foot to the lateral of the foot or be placed on an angle such as from lateral posterior of the foot to medial anterior of the foot.

According to an aspect of some embodiments, a plurality of fluidic conduit may, but need not necessarily, be routed into a fluidic manifold, wherein the fluidic manifold may be freestanding or detachable and/or permanently embedded and/or integrated with the footwear.

According to an aspect of some embodiments, human gait-enabled sequential fluidic actuation of a plurality of fluidic actuators and/or fluidic sensors may, but need not necessarily, be achieved by a plurality of fluidic regenerative chambers spanning the foot from posterior to anterior.

According to an aspect of an embodiment, one or a plurality of fluidic regenerative chambers may, but need not necessarily, be shaped and/or used as wedge-style foot orthotics.

According to an aspect of an embodiment, one or a plurality of fluidic intake mechanisms may, but need not necessarily, be manually controlled by the user, wherein when combined with one or a plurality of one-way flow valves allow fluid to enter the internal closed-loop fluidic regenerative system without backflow out into the external atmosphere.

According to some embodiments, closed-loop fluidic regenerative footwear, apparel, and device may, but need not necessarily, be used as assistive and rehabilitation devices for providing compression, force, torque, and/or any combination thereof to any anatomical body parts. The devices may include but are not limited to knee braces, knee sleeves, orthotics, prosthetics, compression apparel, active footwear, and/or any combination thereof.

According to an aspect of an embodiment, at least one fluidic regeneration chamber within at least one footwear provides fluid pressure and/or volume to at least one fluidic actuator within or be part of a knee brace or knee sleeve via at least one fluidic pathway.

When at least one fluidic actuator is pressurized by the squeezing and/or compression of at least one fluidic regeneration chamber during the stance phase of gait, an unloading mechanism within the knee brace and/or knee sleeve becomes activated and may tighten to offset certain load on the knee or provide a massaging effect. During the swing phase of gait, at least one fluidic actuator may be depressurized as fluidic pressure and/or volume returns to at least one fluidic regeneration chamber. Therefore, the unloading mechanism becomes deactivated, and the unloading force, torque, and/or massaging effect dissipates and/or goes away partially and/or completely. Additional components may be added to the embodiment.

According to an aspect of any embodiments, the fluidic actuator may include but is not limited to Mckibben-type artificial muscle actuator, soft fluidic actuator, balloon actuator, linear pneumatic piston actuator, and/or any combination thereof. Wherein one or a plurality of fluidic conduits may fluidly connect one or a plurality of fluidic actuators with each other.

According to an aspect of some embodiments, one or a plurality of fluidic conduits may fluidly connect one or a plurality of fluidic actuators with one or a plurality of fluidic regeneration chambers.

According to an aspect of an embodiment, human gait-enabled sequential fluidic actuation may enable sequential and/or gradient compression when a closed-loop fluidic regenerative system is combined with at least one active compression sleeve made up of a single or a plurality of compression bands. Wherein one or a plurality of fluidic actuators fluidly connected to a plurality of fluidic regeneration chambers are combined with an active compression sleeve. The plurality of fluidic actuators may not exist underneath the active compression sleeve but rather connects to at least one edge of the sleeve or a plurality of compression bands to tighten it when pressurized.

According to an aspect of an embodiment, a singular active compression sleeve combined with a plurality of soft fluidic actuators may enable sequential and/or gradient compression with the ability to contour over an articulating joint.

According to an aspect of an embodiment, one or a plurality of compression bands combined with one or a plurality of soft fluidic actuators may enable sequential and/or gradient compression with the ability to contour over an articulating joint.

According to an aspect of some embodiments, cooling and/or ice pack that is either passive or active may be applied to the outside of the active compression sleeve and/or one or a plurality of active compression bands to achieve active compression and cooling/icing simultaneously.

According to an aspect of some embodiments, compression bands may, but need not necessarily, overlap each other. Additionally, a single compression band may have different material properties.

According to an aspect of an embodiment, a plurality of fluidic actuators may, but need not necessarily, be connected to at least one connecting plate to allow uniform tension to be applied to the portion and/or section of at least one compression band that connects to at least one connecting plates.

According to an aspect of an embodiment, a single fluidic actuator may, but need not necessarily, loop through at least one connecting plate multiple times in the form of a serpentine and/or zig-zag pattern.

According to an aspect of some embodiments, Cinch™, Velcro™ and/or any strapping mechanism may be employed to enable compression band to enclose and/or wrap around partially and/or the entirety of an anatomical portion of the human body with and/or without gaps.

According to an aspect of an embodiment, a fluidic sensor on a prosthetic socket may be used to sense pistoning, distal-end sinking, motion and/or movement of a residual limb within the prosthetic socket. Wherein at least one fluidic regeneration chamber may be placed between the residual limb and the socket. At least one fluidic conduit connects at least one fluidic regeneration chamber with at least one fluidic sensor. At least one fluidic regeneration chamber may pass on fluid into at least one fluidic sensor to produce visual, audible, tactile, and/or any method to indicate the degree of sinking, pistoning, motion and/or movement of residual limb within the prosthetic socket.

According to an aspect of some embodiments, electromechanical and/or battery-powered systems and/or modules may be added.

Other advantages, features and characteristics of the present invention, as well as methods of operation and functions of the related elements of the structure, and the combination of parts and economies of manufacture, will become more apparent upon consideration of this detailed description with reference to the figures which accompany this application.

BRIEF DESCRIPTION OF THE SEVERAL VIEWS OF THE DRAWINGS

Embodiments of the present disclosure, and related systems and methods, as to their structure, organization, use and method of operation, together with further objectives and advantages thereof, may be better understood from figures which accompany this application, in which embodiments are illustrated by way of example. However, it is expressly understood that any such figures are for the purpose of illustration and description only and are not intended as a definition of the limits of the disclosed subject-matter. In the accompanying figures:

FIG. 3A is a perspective view of a closed-loop fluidic regenerative module with a single fluidic regeneration chamber in accordance with an embodiment described herein;

FIG. 3B is a partial section view of a closed-loop fluidic regenerative module with a single fluidic regeneration chamber in accordance with an embodiment described herein, as seen in FIG. 3A;

FIG. 3C is a close-up detailed section view of a fluidic regeneration chamber when not squeezed/compressed in accordance with an embodiment herein, as seen in FIG. 3B;

FIG. 3D is a close-up detailed section view of a fluidic regeneration chamber when partially and/or completely squeezed/compressed in accordance with an embodiment described herein, as seen in FIG. 3B;

FIG. 12A is a perspective view showing an embodiment described herein, where an active compression sleeve with one or a plurality of compression bands may be connected to one or a plurality of fluidic actuators and/or one or a plurality of connecting plates.

FIG. 12B is a front view showing an embodiment described herein, where a single fluidic actuator may loop through at least one connecting plate multiple times in the form of a serpentine or zig-zag pattern.

FIG. 12C is a perspective view showing an embodiment described herein, where one or a plurality of fluidic actuators may connect to one or a plurality of compression bands directly.

Figure 1:
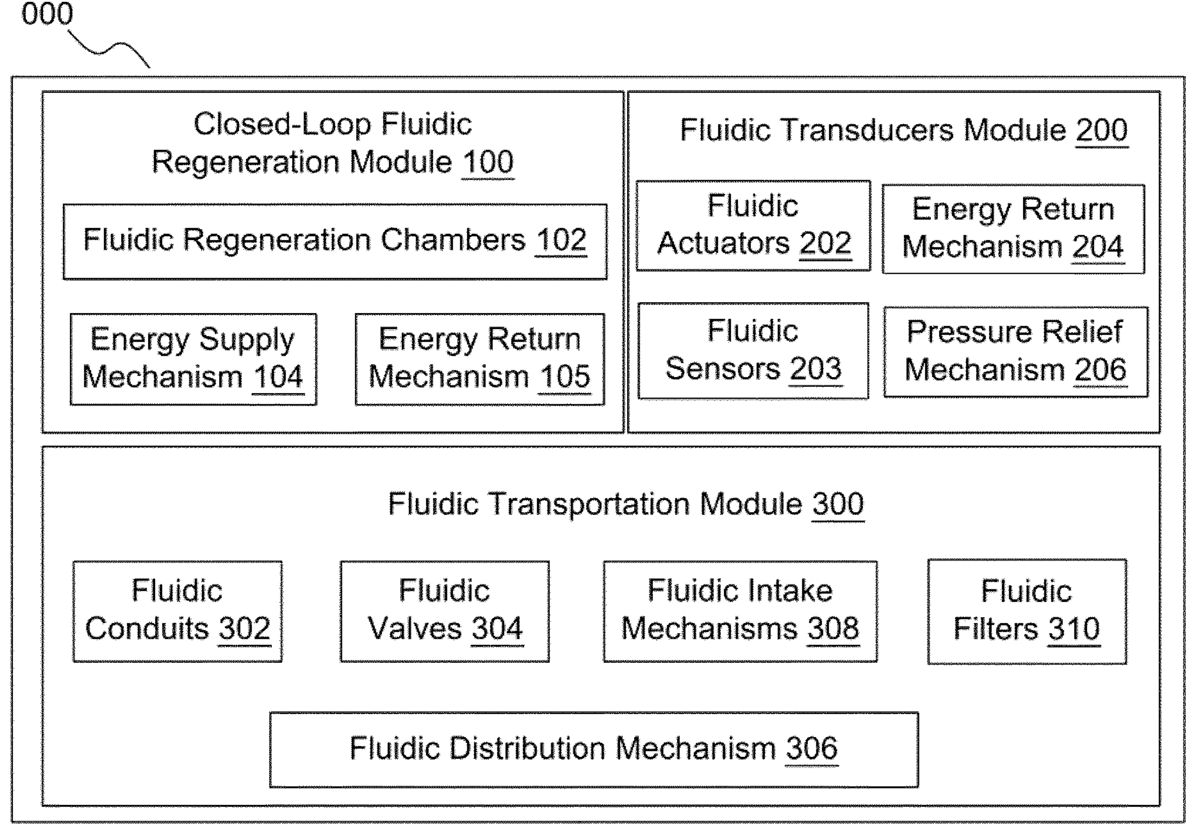
FIG. 1 is a diagram depicting the major modules as well as sub-components of each major module of embodiments described herein.

It is to be understood that the accompanying drawings are used for illustrating the principles of the embodiments and exemplifications of the invention discussed below. Hence the drawings are illustrated for simplicity and clarity, and not necessarily drawn to scale and are not intended to be limiting in scope. Reference characters/numbers are used to depict the elements of the invention discussed that are also shown in the drawings. The same corresponding reference characters/numbers are given to a corresponding component or components of the same or similar nature, which may be depicted in multiple drawings for clarity. Text may also be included in the drawings to further clarify certain principles or elements. It should be noted that features depicted by one drawing may be used in conjunction with or within other drawings or substitute features of other drawings. It should further be noted that common and well-understood elements for creating a commercially viable version of the embodiments of the invention discussed below are often not depicted to facilitate a better view of the principles and elements discussed below.

DETAILED DESCRIPTION OF THE INVENTION

In the following discussion, the accompanying figures pertain to particular embodiments, and the description is not intended to limit the scope, applicability or configuration of the disclosed subject-matter. The description enclosed herein aims to provide any person skilled in the art with the necessary information for the implementation of embodiments of the subject-matter described herein.

Below is some clarification for certain terminologies; it must be noted that the clarifications do not limit the scope of the meaning of the terminologies in the context of the relevant art and the subject-matter described herein.

"Closed-Loop Fluidic Regenerative," "systems," and "device" may be used interchangeably unless explicitly stated otherwise.

"Inflated" and "pressurized" may be used interchangeably unless explicitly stated otherwise.

"Deflated" and "depressurized" may be used interchangeably unless explicitly stated.

"Fluid" may be of any type and/or any mixture of gas, liquid, specialty fluid, magnetic fluid, electrical-driven fluid, Newtonian, non-Newtonian fluid, and indeed any type and/or kind of fluid under any condition, which may include but is not limited to temperature, pressure, compressible and/or incompressible flow, laminar and/or turbulent flow, subsonic and/or supersonic speed.

Singular forms, including but not limited to "a" and "an," may also comprise the meaning of plural forms unless explicitly stated otherwise.

Additionally, plural forms may also comprise the meaning of singular forms unless explicitly stated otherwise.

i. System Overview

Closed-loop fluidic regenerative (CLFR) device, which will be coined as the overall system, comprises numerous major modules, each with numerous sub-components. FIG. 1 is a schematic showing the major modules and their sub-components that make the overall system 000. The major modules are as follows: the closed-loop fluidic regeneration (CLFR) module 100, the fluidic transducers module 200, and the fluidic transportation module 300.

Each major module comprises various sub-components.

The CLFR module 100 comprises the main active components of the overall system 000, including but not limited to fluidic regeneration chambers 102, energy return mechanism 105, and/or energy supply mechanism 104. At least one fluidic regeneration chamber 102 is filled with fluid. The energy supply mechanism 104 is part of the CLFR module 100 that transfers the fluidic pressure and/or volume from at least one fluidic regeneration chamber 102 to other modules and/or sub-components. The energy return mechanism 105 is part of the CLFR module 100 that transfers the fluidic pressure and/or volume from other modules and/or sub-components back to at least one fluidic regeneration chamber 102.

The fluidic transducers module 200 comprises the components that produce and/or sense a variety of motion, movement, torques, and/or forces, achieving rehabilitative, diagnostic, and/or therapeutic effects, including but not limited to fluidic actuators 202, fluidic sensors 203, energy return mechanism 204, and/or pressure relief mechanism 206. At least one fluidic actuator 202 and/or fluidic sensor 203 receives fluidic pressure and/or volume from the CLFR module 100 to produce and/or sense motion, movement, torques and/or forces to itself, another module/sub-component of the overall system 000, coupled device, and/or the user. The energy return mechanism 204 may be part of at least one fluidic actuator 202 and/or fluidic sensor 203 to facilitate the return of fluidic pressure and/or volume from at least one fluidic actuator 202 and/or fluidic sensor 203 to the CLFR module 100. The pressure relief mechanism 206 may be used for safety, which releases excess fluid pressure and/or volume when a certain preset fluidic pressure threshold is reached and/or surpassed.

The fluidic transportation module 300 comprises components that enable fluidic communication between the CLFR module 100 and the fluidic actuators module 200. At least one fluidic conduit 302 provides pathways for fluid to flow from one component to another.

Any number of fluidic valves 304 may control fluid flow by directing flow in a single direction, switching flow pathways, and/or changing flow direction. The fluidic valves 304 may be purely mechanical, meaning no electrical energy is required. The fluidic distribution mechanism 306 acts as a fluidic manifold that allows independent, combined, or mixed fluidic flow between a plurality of fluidic regeneration chambers 102 and a plurality of fluidic actuators 202 and/or fluidic sensors 203. Fluid intake mechanism 308 fills the components that hold fluid of the overall system 000 with initial fluidic pressure/volume; these components include but are not limited to fluidic regeneration chambers 102, fluidic actuators 202, fluidic sensors 203, and various sub-components of fluidic transportation module 300. Fluidic filters 310 may prevent dust, particles, and/or any unwanted elements when filling the overall system 000 with fluid through the fluidic intake mechanism 308.

Any and all of the major modules and/or their subcomponents presented herein may be combined together as one element and/or container or separated into multiple elements and/or containers. Any container enclosing any module and/or their subcomponents may, but need not necessarily, be elastic, flexible, rigid, or any combination thereof. Any and all of the major modules and/or their subcomponents presented herein may be integrated with at least one coupled device in a selectively removable relation.

Various embodiments and exemplifications of the present disclosure are not limited by the major modules and their subcomponents mentioned; additional major modules and any sub-components to any above-mentioned major modules may be added to the overall system 000 to produce commercially-viable versions of the subject-matter described herein. Also, one or more of the above-mentioned major modules and any subcomponents to any above-mentioned major modules may be removed from the overall system 000 to produce commercially viable versions of the subject-matter described herein.

Figure 2:
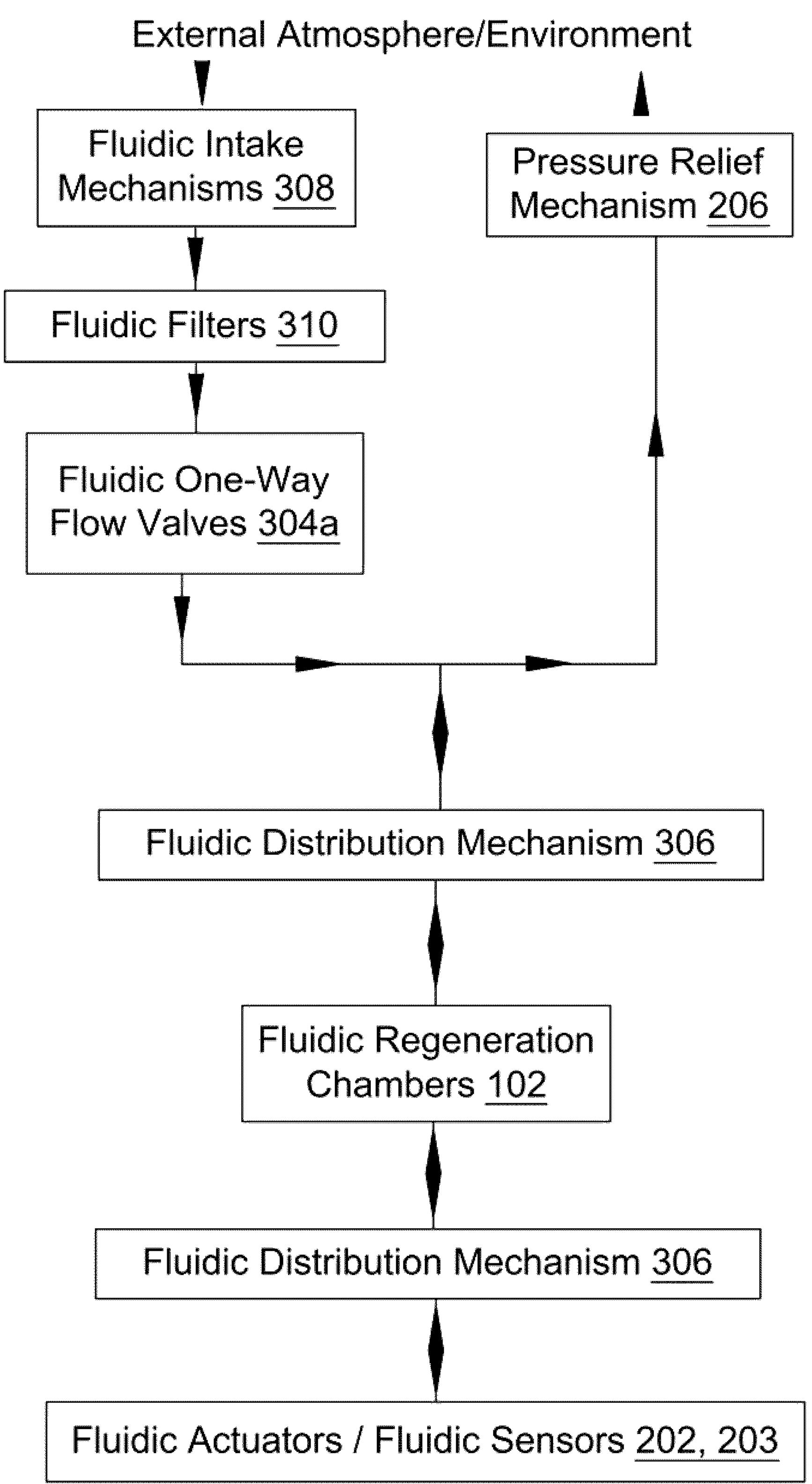
FIG. 2 is a schematic diagram showing the fluid pathways, fluid flow directions, fluidic conduits, and any components involving fluid of embodiments described herein.
Figures 4A, 4B, 4C, 4D:
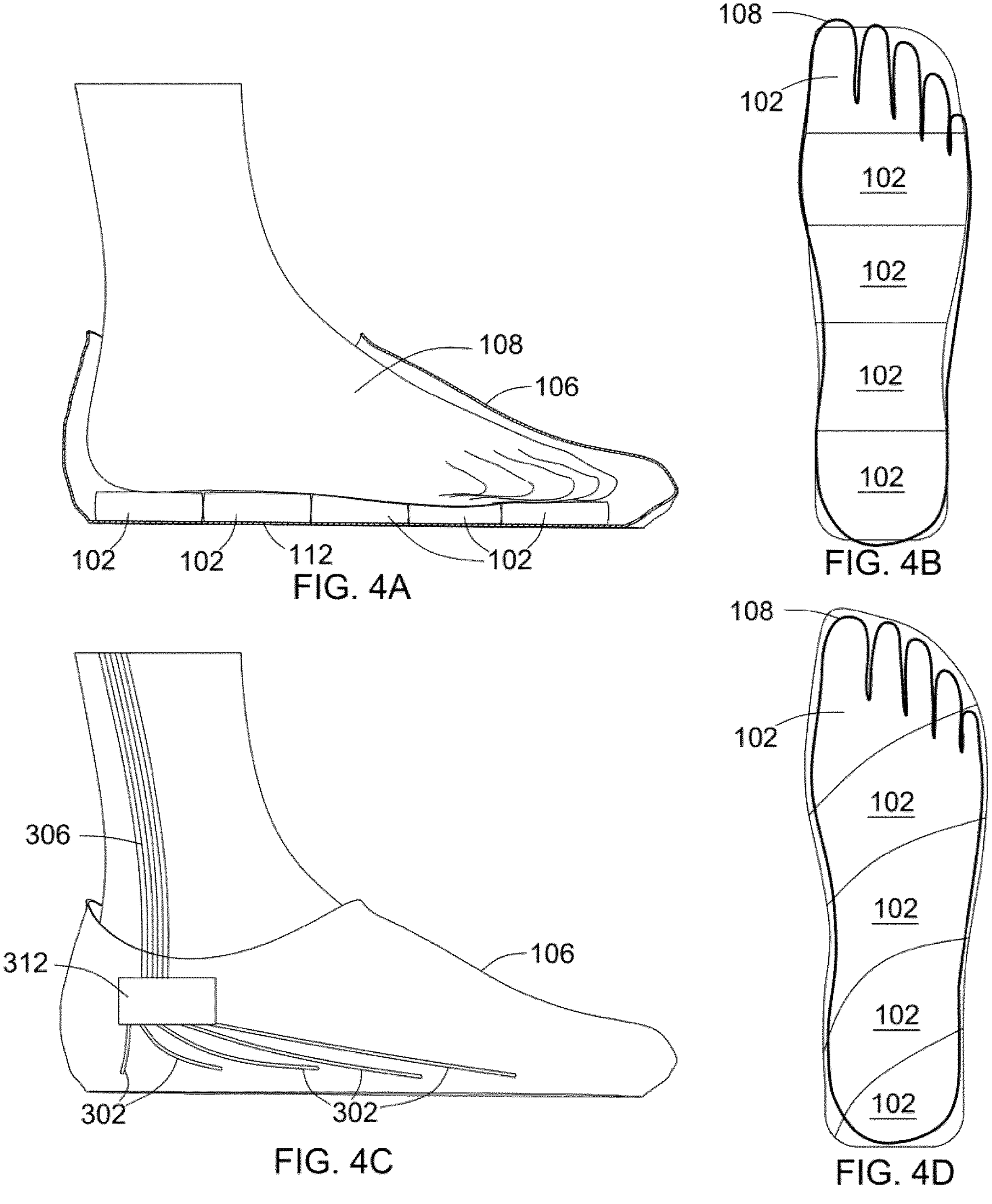
FIG. 4A is a section view of a closed-loop fluidic regenerative module with a plurality of fluidic regeneration chambers in accordance with an embodiment described herein.
FIG. 4B is a bottom view of a plurality of fluidic regeneration chambers, as seen in FIG. 4A.
FIG. 4C is a side view of a closed-loop fluidic regenerative module with a plurality of fluidic regeneration chambers, as seen in FIG. 4A, wherein the fluidic manifold, fluidic conduits, and fluidic distribution mechanism are shown.
FIG. 4D is a bottom view of a plurality of fluidic regeneration chambers placed on an angle as an alternative to the placement shown in FIG. 4B.

FIG. 2 is a general schematic depicting the fluid flow pathways of one or numerous embodiments. Any components mentioned in the schematic herein or not may be added and/or removed from FIG. 2 without deviation from the present disclosure. Any number of any component may exist without departing from the present disclosure. The arrowheads show possible and/or preferred fluid flow directions without limiting any other fluid flow direction. The lines connecting various components may represent at least one fluid pathway/fluidic conduit 302. FIG. 2 may show one possible preferred fluid flow direction of certain embodiments' components regarding upstream and/or downstream relationships from each other. In any embodiment, the location of any components may exist upstream and/or downstream of each other. The purpose of FIG. 2 is to show and demonstrate possible generic fluid flow pathways and directions without limiting possible variations of the fluid flow pathways and directions. The fluidic intake mechanism 308 may push fluid from an external atmosphere/environment into the internal CLFR system. The fluid passes through fluidic filters 310, which removes unwanted particles and/or elements from the fluid. The fluid continues flowing downstream, passing at least one fluidic one-way flow valve 304*a*, which allows fluid to flow in only one direction while preventing backflow upstream. Downstream from at least one fluidic one-way flow valve may exist a fluidic distribution mechanism 306, which may separate a single fluidic conduit/pathway into multiple fluidic conduits/pathways, and/or merge multiple fluidic conduits/pathways into a single one. The two-sided double arrowheads may represent fluidic conduits 302 that may allow fluid to travel in at least two directions (i.e., upstream and/or downstream). At least one fluidic regeneration chamber 102 receives fluid from the fluidic distribution mechanism 306. Another fluidic distribution mechanism 306 may exist between at least one fluidic regeneration chamber 102 and at least one fluidic actuator 202 and/or at least one fluidic sensor 203. Once all the preset amount of fluid (determined by the user or other people including but not limited to medical professionals, healthcare workers, friends, and/or family members) is put into the internal CLFR system, fluid will flow mostly between one or a plurality of fluidic regeneration chambers 102 and at least one fluidic actuator 202 and/or at least one fluidic sensor 203. Suppose fluidic pressure within the internal CLFR system increases above a safe threshold. In that case, the pressure relief mechanism 206 may open up automatically to release the excess fluidic pressure out to the external atmosphere/environment. The pressure relief mechanism 206 may also be manually opened to release fluidic pressure partially or completely out to the external atmosphere/environment. In any embodiments, one or a plurality of fluidic regeneration chambers 102 may be fluidly connected to at least one fluidic actuator 202 and/or at least one fluidic sensor 203.

The CLFR module 100 may be considered the central module that all other modules and sub-components revolve around. The CLFR module 100 and associated components will be described in detail below:

ii. Closed-loop Fluidic Regeneration Module

An embodiment of CLFR module with a single fluidic regeneration chamber 102 is demonstrated in FIG. 3A to FIG. 3D. FIG. 3A shows a perspective view of the CLFR module. The energy supply mechanism 104 creates the energy required to move fluidic pressure and volume from the fluidic regeneration chamber 102 to another part of the internal CLFR system, including but not limited to fluidic actuators, fluidic sensors, fluidic conduits, and/or fluidic distribution mechanism. Some components of other modules are not shown for clarity. As seen in FIG. 3B, the fluidic regeneration chamber 102 may be located inside the footwear 106 between the bottom of the heel of the foot 108 and the inside bottom surface of the footwear 112. The fluidic regeneration chamber 102 may have any shape and/or size and may be placed at any location underneath the foot, depending on the application. The inside bottom surface of footwear 112 includes but is not limited to socks, insole, cushion, orthotics, and/or prosthetics that are part of the footwear or as a removable piece. The energy supply mechanism 104 comprises both components and actions that are produced by the components; the components include but are not limited to leg 110, foot 108, footwear 106, and/or the anatomical kinetic chain (i.e. interrelated groups of body segments, prosthesis, exoskeletons and muscles working together to perform movements, particularly gait). The actions produced by the components include but are not limited to gait, walking, jogging, running, calf raises, and/or any motion/movement that puts pressure on the bottom of the foot. The pressure on the bottom of the foot squeezes/compresses the fluidic regeneration chamber 102 against another surface, including but not limited to the inside bottom surface of the footwear 112 and/or the ground. When the fluidic regeneration chamber 102 is partially and/or completely squeezed/compressed, as seen in FIG. 3D, the fluid within the fluidic regeneration chamber 102 is displaced into another part of the internal CLFR system. The arrows in FIG. 3C and FIG. 3D show the direction of motion of the energy supply mechanism 104. For clarity, fluidic conduits 302, which carry the displaced fluid to and from fluidic regeneration chamber 102, are not shown in FIG. 3C and FIG. 3D. The fluidic conduits 302 include but are not limited to tubing, pipes, microfluidic channels, fluidic channels, and/or any combination thereof. The fluidic conduits 302 may be rigid, flexible, elastic, and/or any combination thereof. The energy return mechanism 105 creates the energy required to move fluidic pressure and/or volume from another part of the internal CLFR system to the fluidic regeneration chamber 102. The energy return mechanism 105 comprises both components and actions that are produced by the components; the components include but are not limited to leg 110, foot 108, footwear 106, spring 114, which is part of the fluidic regeneration chamber 102 (FIG. 3C), wall 116 which is part of the fluidic regeneration chamber (FIG. 3C) and/or the anatomical kinetic chain (i.e. interrelated groups of body segments, prosthesis, exoskeleton and muscles working together to perform movements, particularly gait). The actions produced by the components include but are not limited to gait, walking, jogging, running, calf raises, and/or any motion/movement that lifts pressure off the bottom of the foot. When the energy return mechanism 105 releases the pressure on the bottom of the foot, the fluidic regeneration chamber 102 returns to a partial and/or completely relaxed state, whereby the displaced fluid during a partial and/or completely squeezed/compressed state returns to the fluidic regeneration chamber 102. The release of pressure on the bottom of the foot directly over the fluidic regeneration chamber 102 may often be created when the bottom of the foot directly over the fluidic regeneration chamber 102 is during the motion or the state of not contacting the ground, for instance, the swing phase of gait. At least one spring 114 may facilitate fluid return into the fluidic regeneration chamber by helping open up the inside volume of the fluidic regeneration chamber 102 by pushing against at least two sides of the fluidic regeneration chamber 102. At least one spring 114 may be anything material and/or thing that produces elastic potential energy when deformed in any way. In certain embodiments of the present invention, spring 114 may not exist. At least one wall 116 of the fluidic regeneration chamber 102 may be elastic, flexible, rigid, and/or any combination thereof. At least one wall 116 separates the internal environment of the fluidic regeneration chamber 102 and contains the fluid within, and has at least one port to at least one fluidic conduit 302. The fluidic conduit 302 may be permanently, detachably, and/or semi-permanently connected to the port on wall 116 of the fluidic regeneration chamber 102. At least one wall 116 may act as the spring for the energy return mechanism 105. The completely relaxed state of the fluidic regeneration chamber 102 may have fluidic pressure above the external environment pressure. In certain embodiments of the present invention, footwear may not be necessary, and/or the fluidic regeneration chamber 102 may be contacting the ground directly, and/or one or a plurality of prosthesis, and/or a part of one or a plurality of prosthesis and/or the fluidic regeneration chamber 102 may be contacting the outside bottom surface of the footwear.

An embodiment of CLFR module with a plurality of fluidic regeneration chambers (FRC) 102 is demonstrated in FIG. 4A to FIG. 4D. Fluidic conduits are not shown in FIG. 4A and FIG. 4B for clarity. Also, some components of other modules are not shown for clarity. The overall working principle of a CLFR module with a plurality of FRCs 102 is the same as that of a CLFR module with a single FRC, as shown in FIG. 3. Depicted by FIG. 4A and FIG. 4B, a plurality of FRCs 102 are preferably placed along the span of the foot from the heel to the tip of the toe (the advantage of this placement will be discussed in detail in the paragraph (s) detailing FIG. 5). In certain embodiments of the present invention, the plurality of FRC 102 may alternatively be placed from the medial of the foot to the lateral of the foot or placed on an angle (FIG. 4D) such as from lateral posterior of the foot to medial anterior of the foot. Due to the curvature and irregular shape of the bottom of the foot, the size, height, and/or shape of each FRC 102 may be different for a better fit or to achieve a certain amount of fluidic volume and/or pressure when squeezed/compressed by the energy supply mechanism. The inside bottom surface of the footwear may also have contours and/or irregular shapes to better facilitate the energy supply mechanism to squeeze/compress the plurality of FRC 102. In a preferred embodiment of the present invention, each FRC 102 is fluidly independent of another FRC 102 which means that each FRC 102 requires an independent fluidic conduit 302 to deliver fluidic pressure/volume to its respective fluidic actuators/sensors. The plurality of fluidic conduits 302 may be routed into a fluidic manifold 312 and into a fluidic distribution mechanism 306, which combines multiple independent fluidic conduits 302 into a single tether, which may house multiple independent fluidic conduits to minimize freestanding fluidic conduits 302. The fluidic conduits 302 from each FRC 102 leading to the fluidic manifold 312 may be freestanding or detachably and/or permanently embedded and/or integrated with the footwear 106. Holes may be created on the surface of the footwear 106 to allow fluidic conduits 302 to pass through. In certain embodiments, the fluidic conduits 302 may be detachably and/or permanently embedded and/or integrated with the footwear 106. Part or the whole of the fluidic distribution mechanism 306 and/or fluidic manifold 312 may be detachably and/or permanently embedded and/or integrated with the footwear 106.

Figures 5A, 5B, 5C, 5D, 5E:
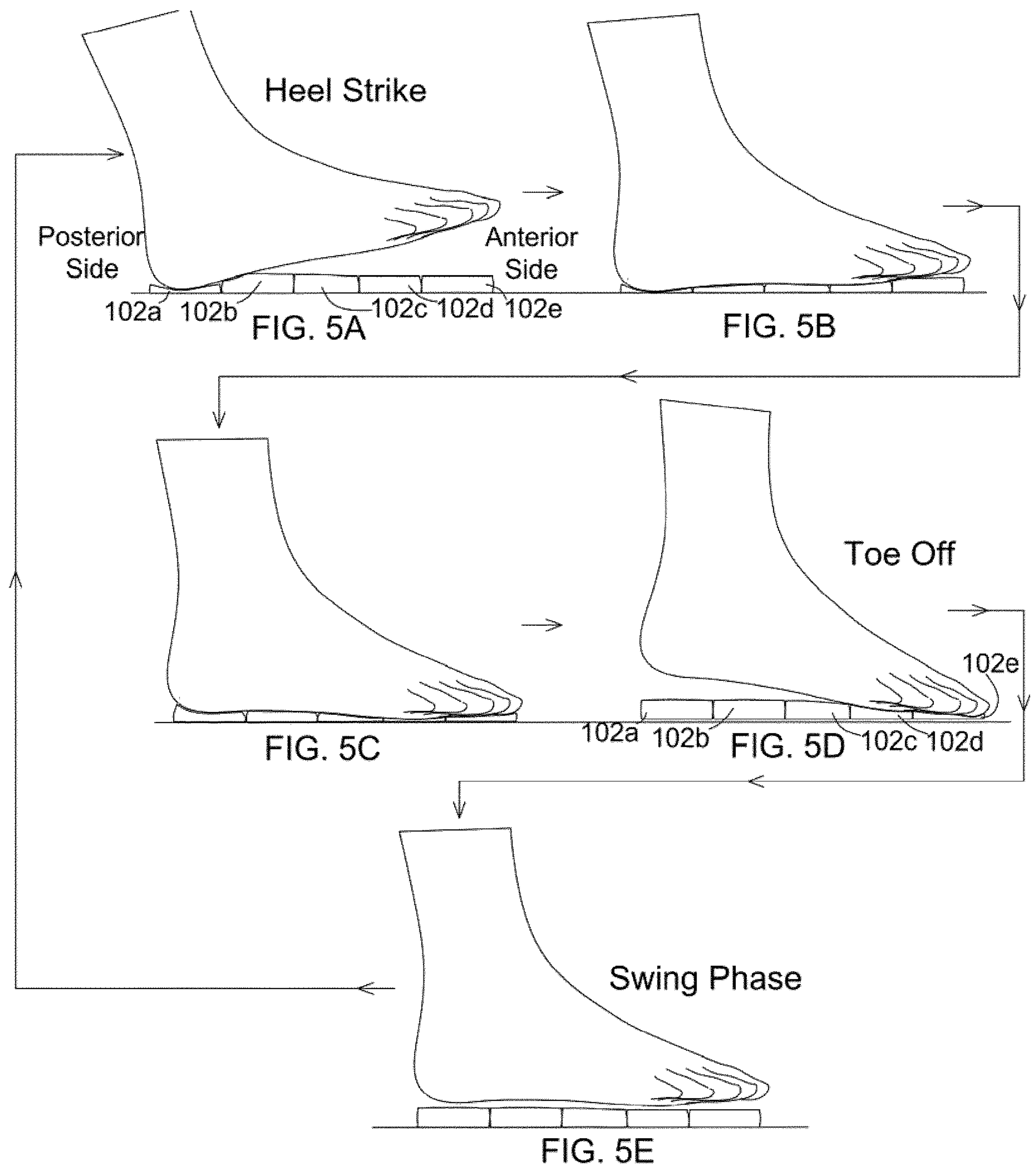
FIG. 5A to FIG. 5E together presents a diagram depicting the human gait-enabled sequential fluidic actuation enabled with a plurality of fluidic regeneration chambers.

FIG. 5A to FIG. 5E is a diagram depicting the human gait-enabled sequential fluidic actuation. Please note that FIG. 5A to FIG. 5E are diagrams meant to be viewed together, and for clarity, the orientation and gaps between the foot and FRC are exaggerated and/or not to scale. Please also note that footwear, fluidic conduits, and other sub-components of the CLFR module as well as other modules are not shown in FIG. 5A to FIG. 5E for clarity. The arrows show the progression of the gait cycle from the heel strike (FIG. 5A) to the swing phase (FIG. 5E). Human gait-enabled sequential fluidic actuation takes advantage of human biomechanics, particularly gait, where during the stance phase, the heel strikes the ground first followed by the midfoot, and then the forefoot. Immediately after, the heel lifts off from the ground first, followed by the midfoot, and then the forefoot into the swing phase. When a plurality of FRCs is placed underneath the foot from the back (posterior) to the front (anterior) of the foot, the FRC 102*a* that is the most posterior may be the first to be squeezed/compressed, followed by the FRC 102*b* next to it that is more anterior, and this pattern continues until the FRC 102*e* that is the most anterior is squeezed/compressed. Based on the reference numbers as shown in FIG. 5A, the sequence of FRC being squeezed/compressed would be 102*a*, followed by 102*b*, then 102*c*, then 102*d*, and lastly 102e. FIG. 5B shows that multiple FRCs could be squeezed/compressed simultaneously by the same or different amount. FIG. 5C shows that all FRC could be squeezed/compressed simultaneously by the same or different amount. FIG. 5D shows the toe-off moment of the stance phase where some FRC 102*a*, 102*b* closer to the posterior are not squeezed/compressed fully or partially. FRC 102*c* at around the midfoot may only be slightly squeezed/compressed. FRC 102*d*, 102*e* closer to the anterior are simultaneously squeezed/compressed fully or partially. FIG. 5E shows the swing phase where the foot is not contacting the ground, and hence all FRC are not squeezed/compressed fully or partially. After the swing phase, the stance phase occurs again, and the cycle repeats. During the swing phase of one foot, the other foot may squeeze/compress a plurality of FRC to continue the human gait-enabled sequential fluidic actuation without a gap between cycles of sequential fluidic actuation.

Figures 6, 7A, 7B:
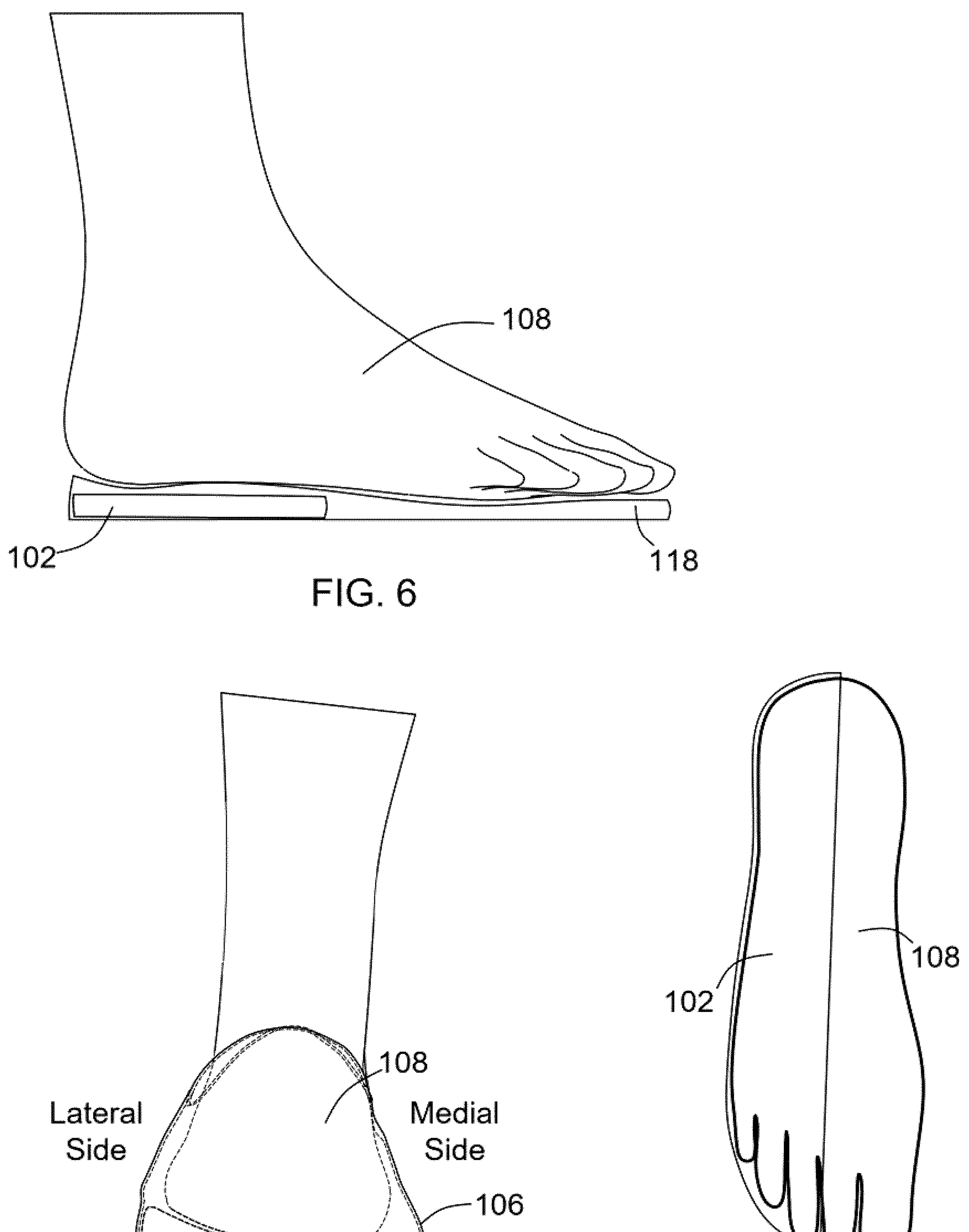
FIG. 6 is a side view showing one or a plurality of fluidic regeneration chambers integrated with one or a plurality of housing, which may include but is not limited to a cushion, insole, orthotics, prosthetics, apparel, footwear, and/or any combination thereof.
FIG. 7A is an anterior view showing at least one fluidic regenerative chamber in the shape of or used as a wedge-style foot orthotics in accordance with an embodiment described herein.
FIG. 7B is a top view showing at least one fluidic regenerative chamber in the shape of or used as a wedge-style foot orthotics, as seen in FIG. 7A.

As shown in FIG. 6, in certain embodiments, one or a plurality of FRCs 102 may be embedded within one or a plurality of housings 118, which may include but not limited to a cushion, insole, orthotics, prosthetics, apparel, footwear, and/or any combination thereof. Embedding FRCs 102 within housings 118 may improve user comfort by providing a smoother transition between the FRCs 102 and the footwear. For clarity, please note that footwear, fluidic conduits, and other sub-components of CLFR module and/or other modules are not shown in FIG. 6.

FIG. 7A and FIG. 7B show an embodiment wherein at least one FRC 102 may be shaped and/or used as a wedge-style foot orthotics. Please note certain components, including but not limited to fluidic conduits, are not shown in FIG. 7A and FIG. 7B for clarity. The FRC-enabled wedge-style foot orthotics may be placed on the lateral side, medial side, anterior side, posterior side, and/or any combination thereof within footwear 106. In certain embodiments, multiple FRC-enabled wedge-style foot orthotics may be placed within footwear 106. The FRC-enabled wedge-style foot orthotics may be used to dynamically realign or stabilize the foot 108 and skeletal structure during gait or lower body movement while providing fluidic pressure and/or volume to the fluidic actuators and/or fluidic sensors.

Figure 8:
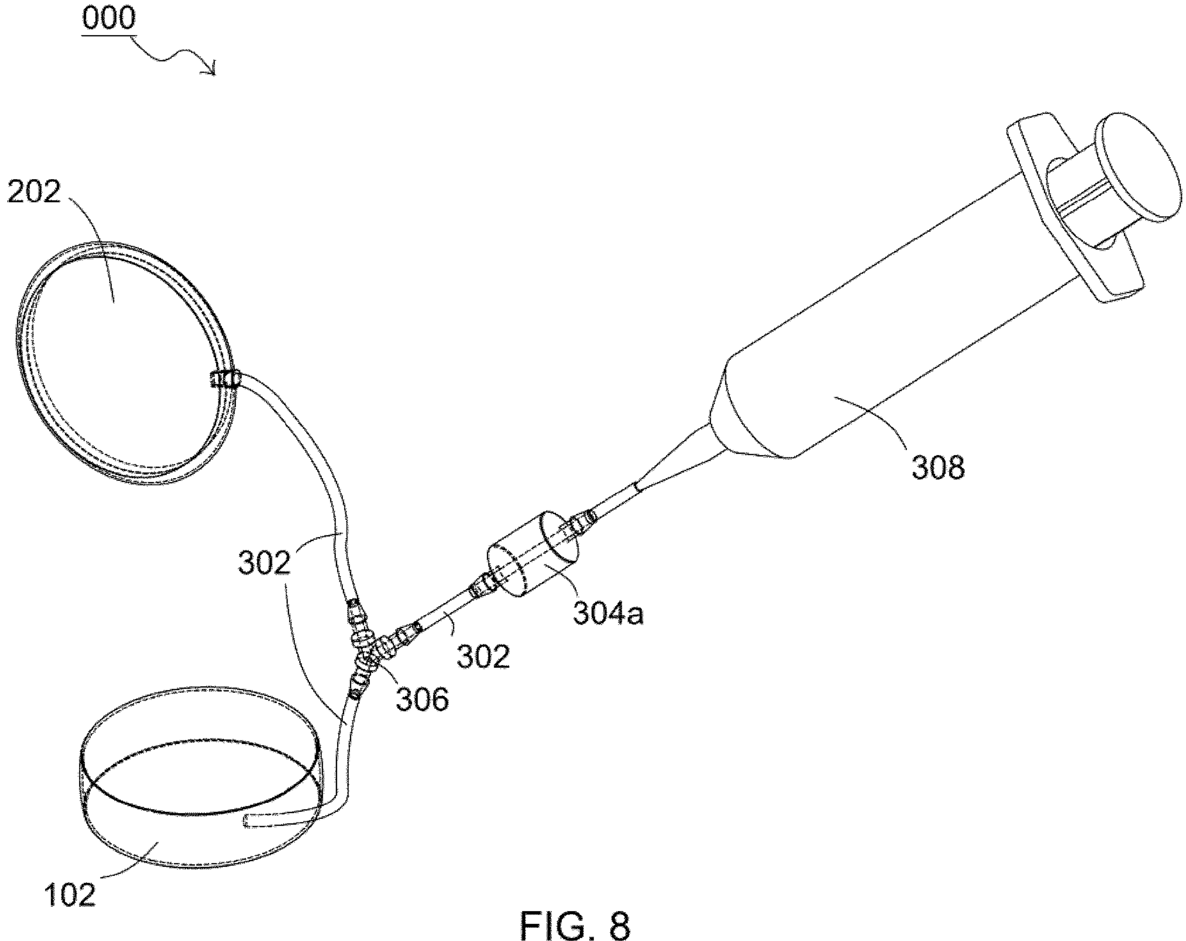
FIG. 8 is a perspective view showing the fluid communications of the overall system between the closed-loop fluidic regeneration module, the fluidic actuators/sensors module, and the fluidic transportation module in accordance with an embodiment described herein.

FIG. 8 is a diagram showing the fluid communications of the overall system 000 between the CLFR module, the fluidic actuators module, and the fluidic transportation module. The diagram is meant to convey the functional purposes of each component clearly and not limit the physical features of each component. A fluidic distribution mechanism 306 may fluidly connect any number of FRC 102 with any number of fluidic actuators 202 and/or fluidic sensors 203 and/or any number of fluidic intake mechanisms 308. A fluidic distribution mechanism 306 may also connect the aforementioned components with any number of valves which include but are not limited to fluidic one-way flow valves 304*a* and/or fluidic pressure relief valves. Any components may be added to or removed from the overall system 000. The physical appearance of each component described herein for various embodiments may differ from those shown in FIG. 8. Fluidic conduits 302 may connect to fluidic distribution mechanism 306 permanently and/or detachably. All sub-components of the overall system 000 may connect permanently and/or detachably to each. At least one fluidic intake mechanism 308 may connect to a fluidic one-way flow valve 304*a* to fill the internal CLFR system with fluid. The fluidic intake mechanism 308 may be a detachable syringe-type device or a device integrated with the fluidic one-way flow valve 304*a*. The fluidic intake mechanism 308 may be manually controlled by the user. The fluidic one-way flow valve 304*a* allows fluid to enter the internal CLFR system without backflow out into the external atmosphere. A fluidic pressure relief valve may also be integrated with the fluidic one-way flow valve 304*a*. The fluidic pressure relief valve may be opened manually to release fluidic pressure and/or volume from the internal CLFR system into the external atmosphere. In cases of over-pressurization of the internal CLFR system, the fluidic pressure relief valve may automatically open up to release pressure until a safe threshold is achieved and at which point, the fluidic pressure relief valve may be automatically closed. The fluidic distribution mechanism 306 may also be integrated with the fluidic one-way flow valve 304*a*. Some components may be combined and/or integrated into a single container.

iii. Applications

CLFR footwear, apparel, and device may be used as assistive and/or rehabilitation devices for providing compression, force, torque, and/or any combination thereof to any anatomical body parts. CLFR devices include but are not limited to knee braces, knee sleeves, orthotics, prosthetics, compression apparel, active footwear, and/or any combination thereof. Below may be some example embodiments related to certain applications described herein.

Figures 9A, 9B:
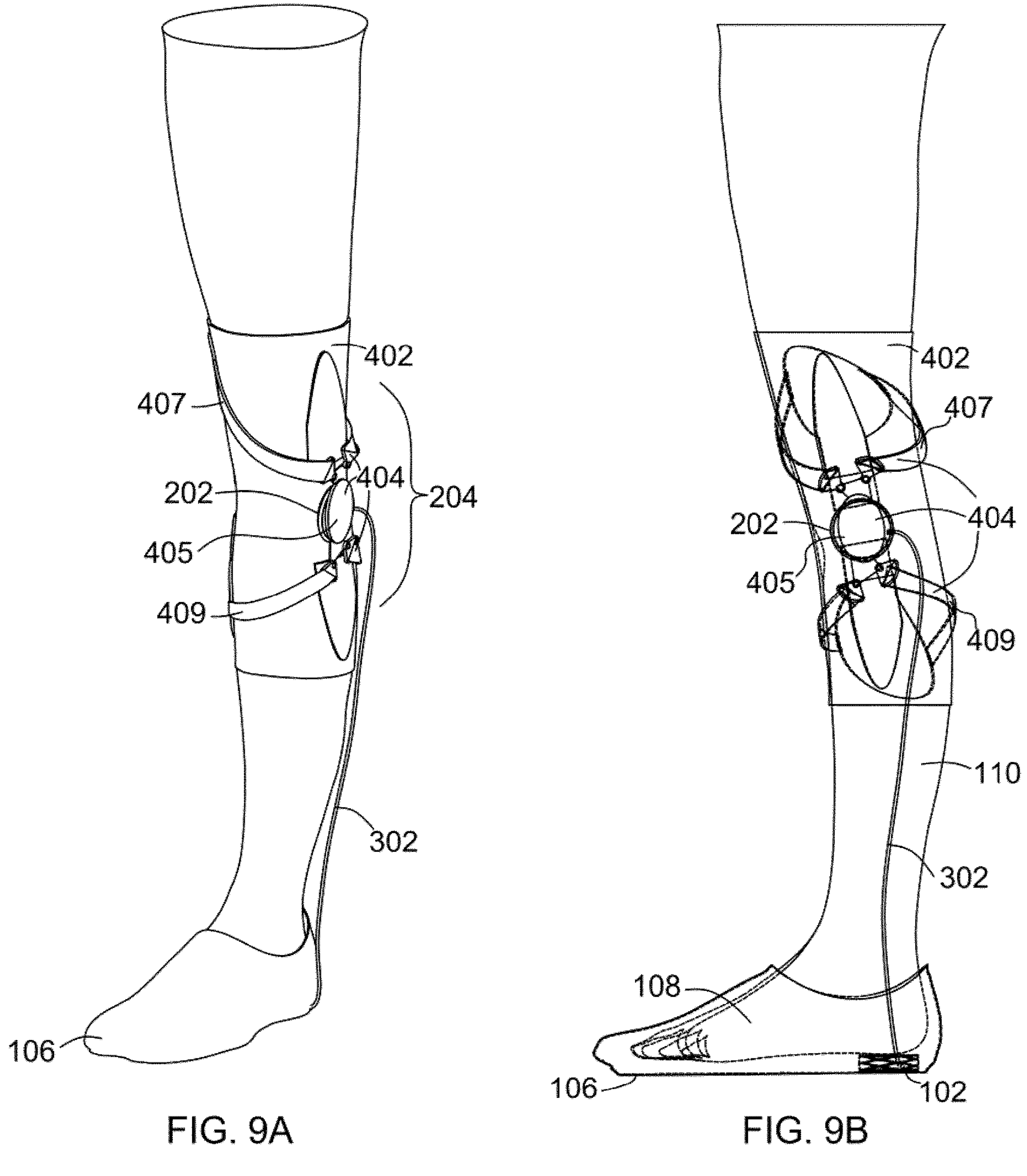
FIG. 9A is a perspective view showing an embodiment described herein, where the closed-loop fluidic regenerative system is used to enable an active knee brace/knee sleeve.
FIG. 9B is a side view showing an embodiment where the closed-loop fluidic regenerative system is used to enable an active knee brace/knee sleeve, as seen in FIG. 9A.

FIG. 9A and FIG. 9B shows one application where the CLFR system is used to enable an active knee brace/knee sleeve. The active knee brace/knee sleeve 402 may provide unloading and/or massage to the knee dynamically during gait and/or lower extremity movement. At least one FRC 102 within the footwear 106 provides the fluid pressure and/or volume to at least one fluidic actuator 202 via at least one fluidic pathway, which may be any number of fluidic conduits 302, any number of fluidic distribution mechanisms and/or any combination thereof. At least one fluidic conduit 302 may connect to at least one fluidic actuator 202 detachably and/or permanently via at least one port. The entirety or a part of the knee brace/knee sleeve 402 may be the energy return mechanism 204, which may act as a spring to squeeze/compress the fluid pressure and/or volume within at least one fluidic actuator 202 back to at least one FRC 102. In certain embodiments, at least one wall of the fluidic actuator 202 may also act as part of the energy return mechanism 204. For instance, in certain medial compartment unloading knee braces/knee sleeves 402 for reducing external knee abduction moment (KAM) for managing medial compartment osteoarthritis as shown in FIG. 9A and FIG. 9B, at least one fluidic actuator 202 may detachably and/or permanently be attached to part of the 3-point unloading mechanism 404 comprising an articulation joint 405, an upper strap 407, and a lower strap 409, each coupled with the articulation joint 405 and respectively extending to encompass a lower end of the upper leg, and an upper end of the lower leg. When the fluidic actuator 202 is inflated/pressurized, the articulation joint 405 may expand or backstop the fluidic actuator 202 to apply pressure to an outside surface of the knee. At the same time, the upper strap 407 and the lower strap 409 may be tightened about the leg by the outward movement of the articulation joint 405. Such applications of pressure may decrease KAM. Please note fluidic valves, fluidic intake mechanism, fluidic filters, and pressure relief mechanism are not shown in FIG. 9 but may be incorporated into any embodiments. The advantage over traditional static knee braces/knee sleeves is the dynamic feature where the fluidic actuator 202 is only inflated/pressured to tighten the 3-point unloading mechanism 404 when needed to improve comfort, proprioception, user compliance, and/or function. For instance, unloading is generally only necessary during the stance phase of gait when the knee is usually bearing weight, and not necessary during the swing phase of gait when the knee is generally not bearing weight. Therefore, at least one fluidic actuator 202 may be inflated/pressurized by at least one FRC 102 starting at heel strike when at least one FRC 102 starts to be squeezed/compressed by the energy supply mechanism of the CLFR module which includes but are not limited to the foot 108 and leg 110 and through part and/or entire duration of the stance phase as long as at least one FRC 102 is squeezed/compressed partially and/or completely. During the swing phase of gait, the energy return mechanism of the CLFR module and/or the fluidic actuators module partially and/or completely deflates/depressurizes at least one fluidic actuator 202 by returning fluid pressure and/or volume back to at least one FRC 102. Overall, the fluidic actuator 102 may only be inflated/pressurized by the CLFR module during weight-bearing activities, which means the 3-point unloading mechanism is only tightened to reduce KAM during weight-bearing activities. In certain embodiments of the present invention, the 3-point unloading mechanism may be tightened to a baseline tightness and/or at least one fluidic actuator 202 and/or at least one FRC 102 is inflated/pressurized to a baseline pressure/volume and any further inflation/pressurization of the at least one fluidic actuator 202 and/or at least one FRC 102 further increases the tightness of the 3-point unloading mechanism. In certain embodiments, during the swing phase of the gait or when the footwear 106 and/or the foot 108 is not contacting the ground, the FRC 102 may still be squeezed/compressed partially, which may be due to many reasons including but not limited to the fact that the footwear 106 may be too tight on the foot which limits the volume or how much at least one FRC may expand when filling with fluid.

Figure 10:
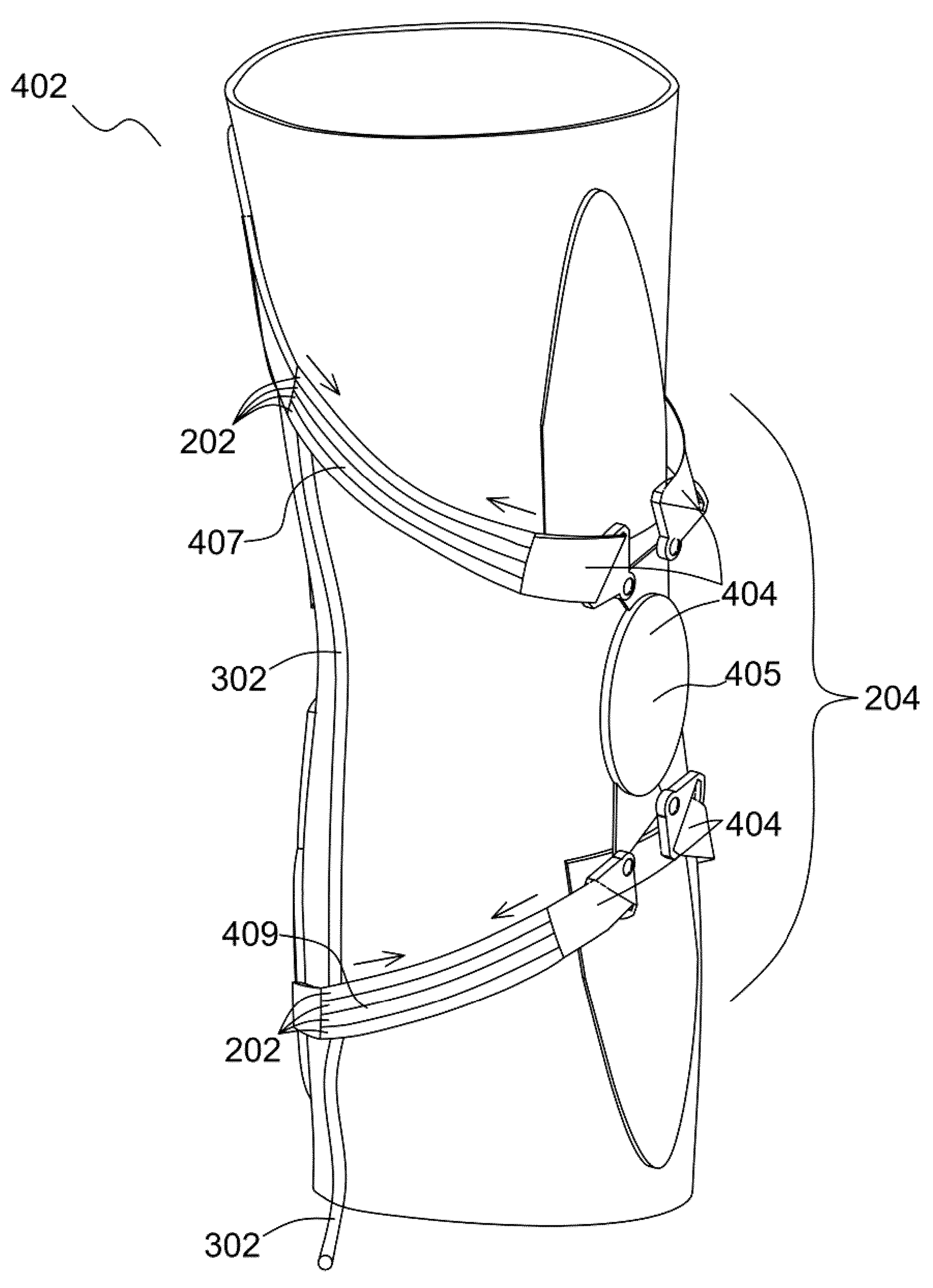
FIG. 10 is a perspective view showing yet another embodiment described herein, where the closed-loop fluidic regenerative system is used to enable an active knee brace/knee sleeve.

FIG. 10 shows another embodiment of the present invention where an unloader-type knee brace/knee sleeve 402 is combined with a plurality of fluidic actuators 202 that are actuated by the CLFR module. Different from the embodiment shown in FIG. 9, the plurality of fluidic actuators 202 are part of the straps 407, 409 of the 3-point bending mechanism 404. When the plurality of fluidic actuators 202 is inflated/pressurized, they contract in the direction of the arrowheads, which tightens the straps and tightens the 3-point mechanism 404. Similar to the embodiment shown in FIG. 9, the entirety or a part of the knee brace/knee sleeve 402 may be the energy return mechanism 204, which may act as a spring to stretch at least one fluidic actuator 202, which causes fluid pressure and/or volume within at least one fluidic actuator 202 to flow back to at least one FRC (not shown in FIG. 10 for clarity). In certain embodiments of the present invention, at least one wall of the fluidic actuator 202 may also act as part of the energy return mechanism 204. The fluidic actuators 202 may be rigid, flexible, elastic, and/or any combination thereof for any of the embodiments of the present invention. The fluidic actuators 202 may include but are not limited to Mckibben-type artificial muscle actuator and/or soft fluidic actuator, linear pneumatic piston actuator, and/or any combination thereof for any of the embodiments. One or a plurality of fluidic conduits 302 may fluidly connect one or a plurality of fluidic actuators 202 with each other and/or one or a plurality of FRC. Other sub-components of the fluidic transportation module may also be included.

iv. Active Compression Bands

Figure 11A:
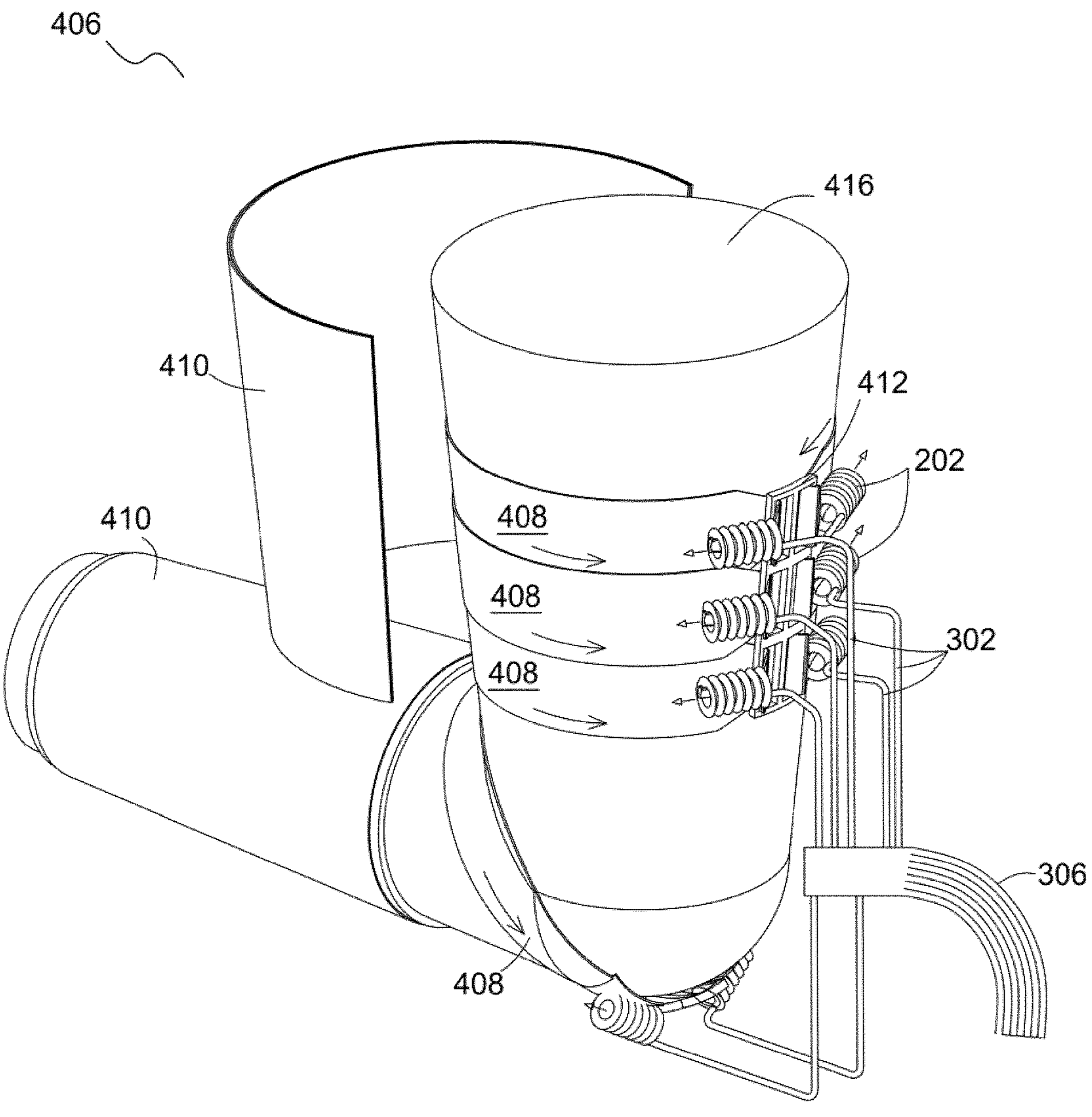
FIG. 11A is a perspective view showing an embodiment described herein, where the closed-loop fluidic regenerative system is used to enable an active compression sleeve.
Figures 11B, 11C:
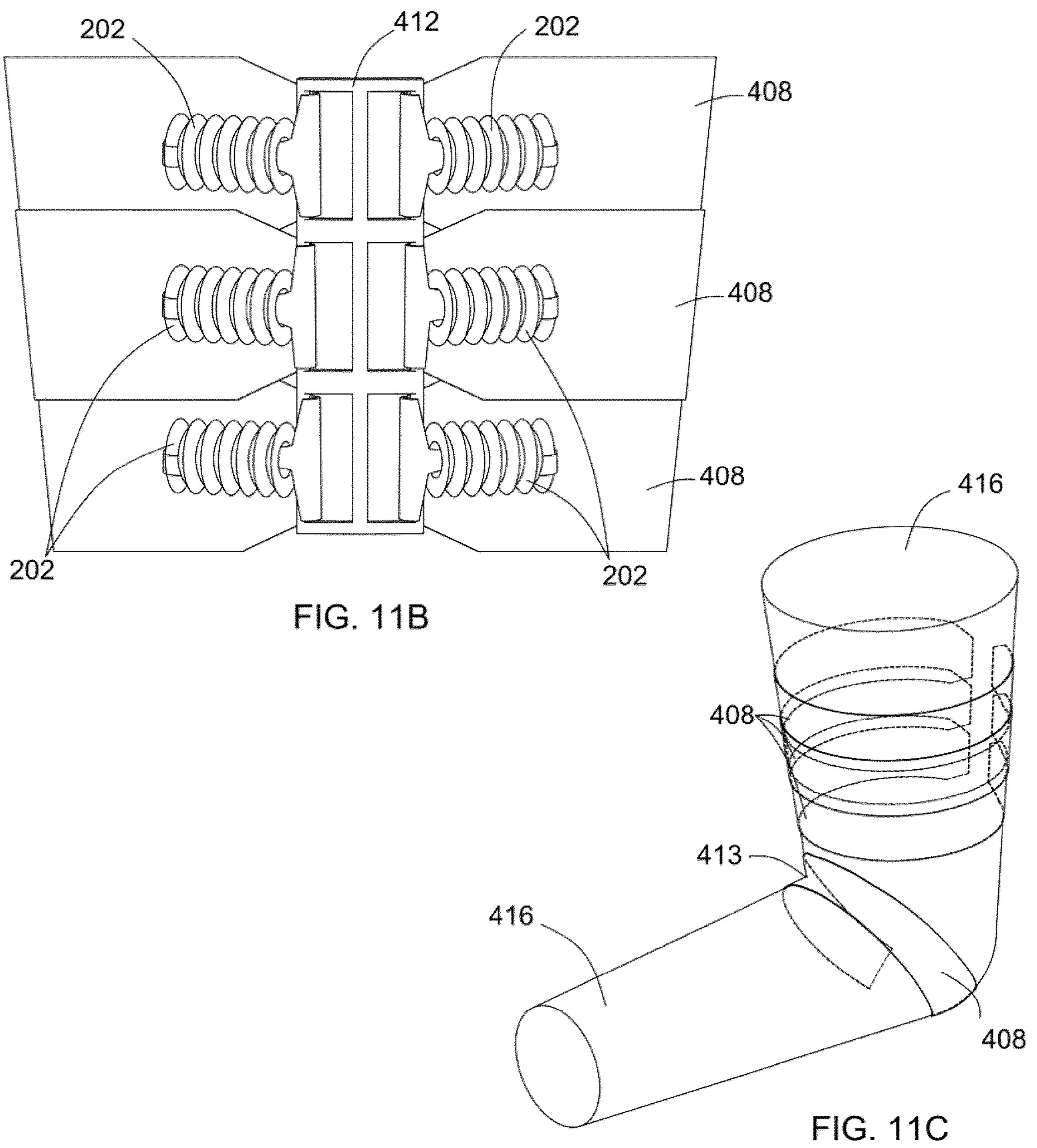
FIG. 11B is a close-up view of the fluidic actuator and associated components of the embodiment shown in FIG. 11A.
FIG. 11C shows the compression band without other components for clarity of the embodiment shown in FIG. 11A.
Figure 11D:
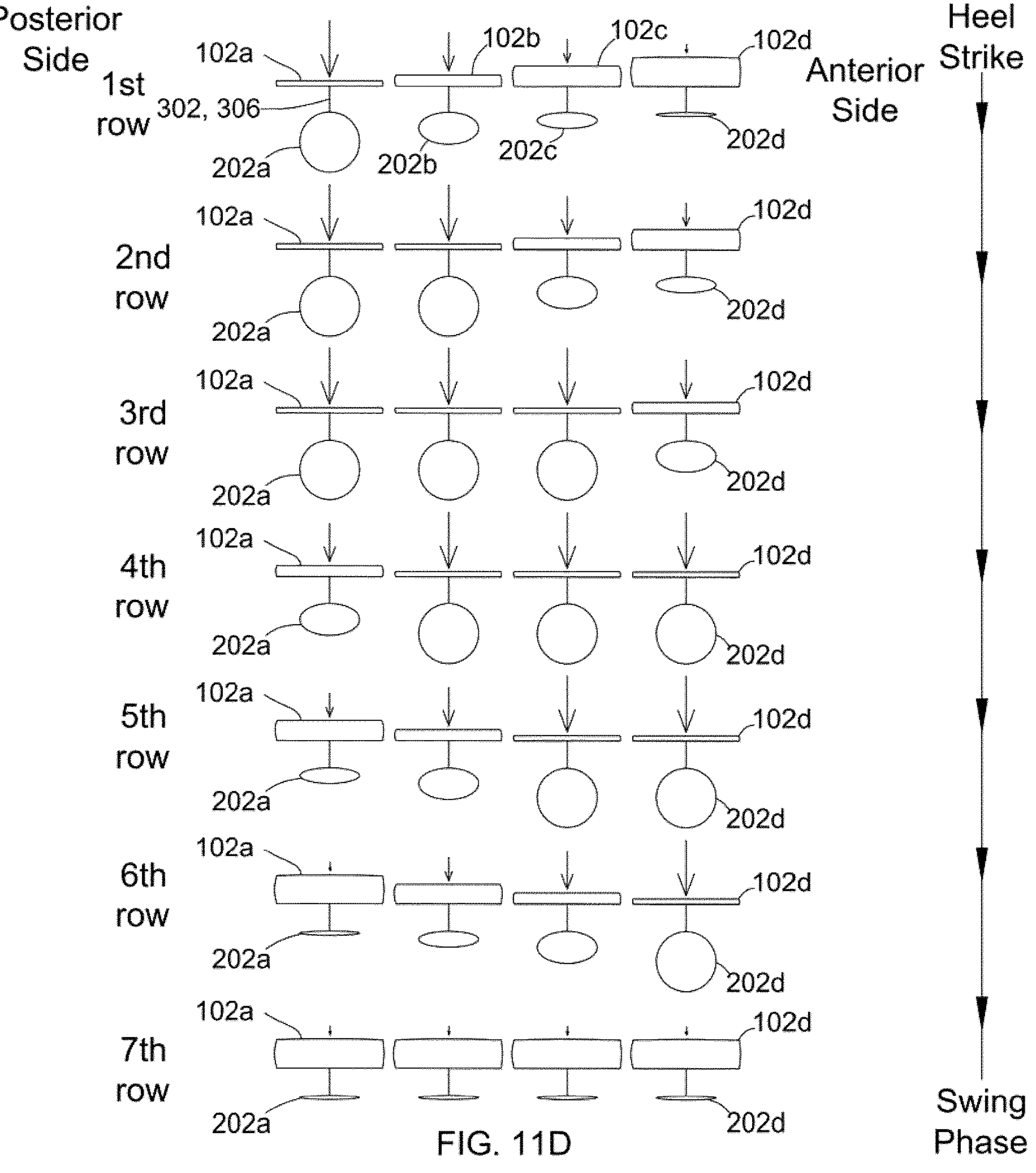
FIG. 11D is a schematic diagram showing how a plurality of fluidic regeneration chambers may sequentially activate a plurality of fluidic actuators to produce sequential gradient compression with at least one active compression band as described herein.
Figure 13A:
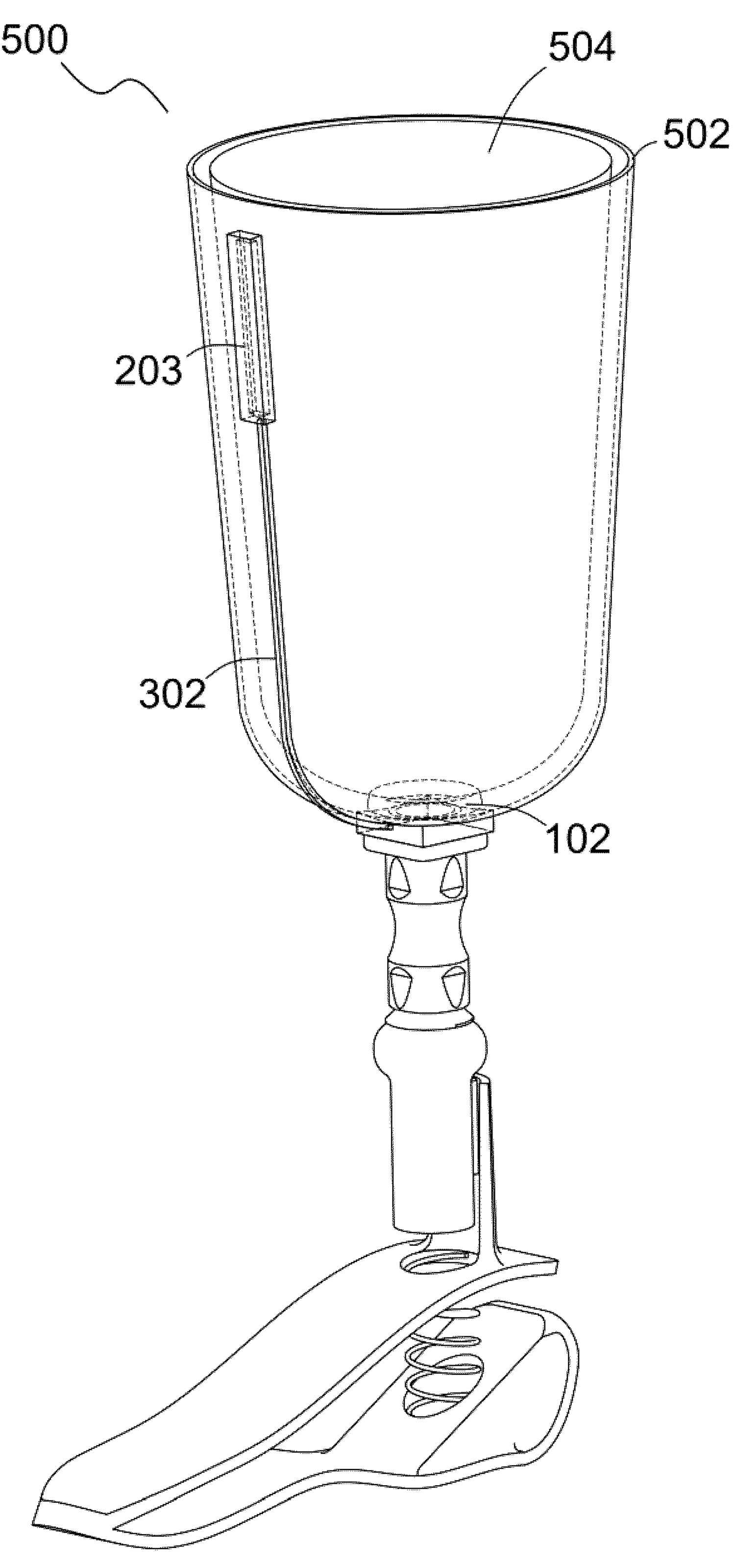
FIG. 13A is a perspective view showing an embodiment described herein, where the closed-loop fluidic regenerative system is used to enable fluidic sensors to detect socket fit for prostheses.
Figures 13B, 13C, 13D, 13E:
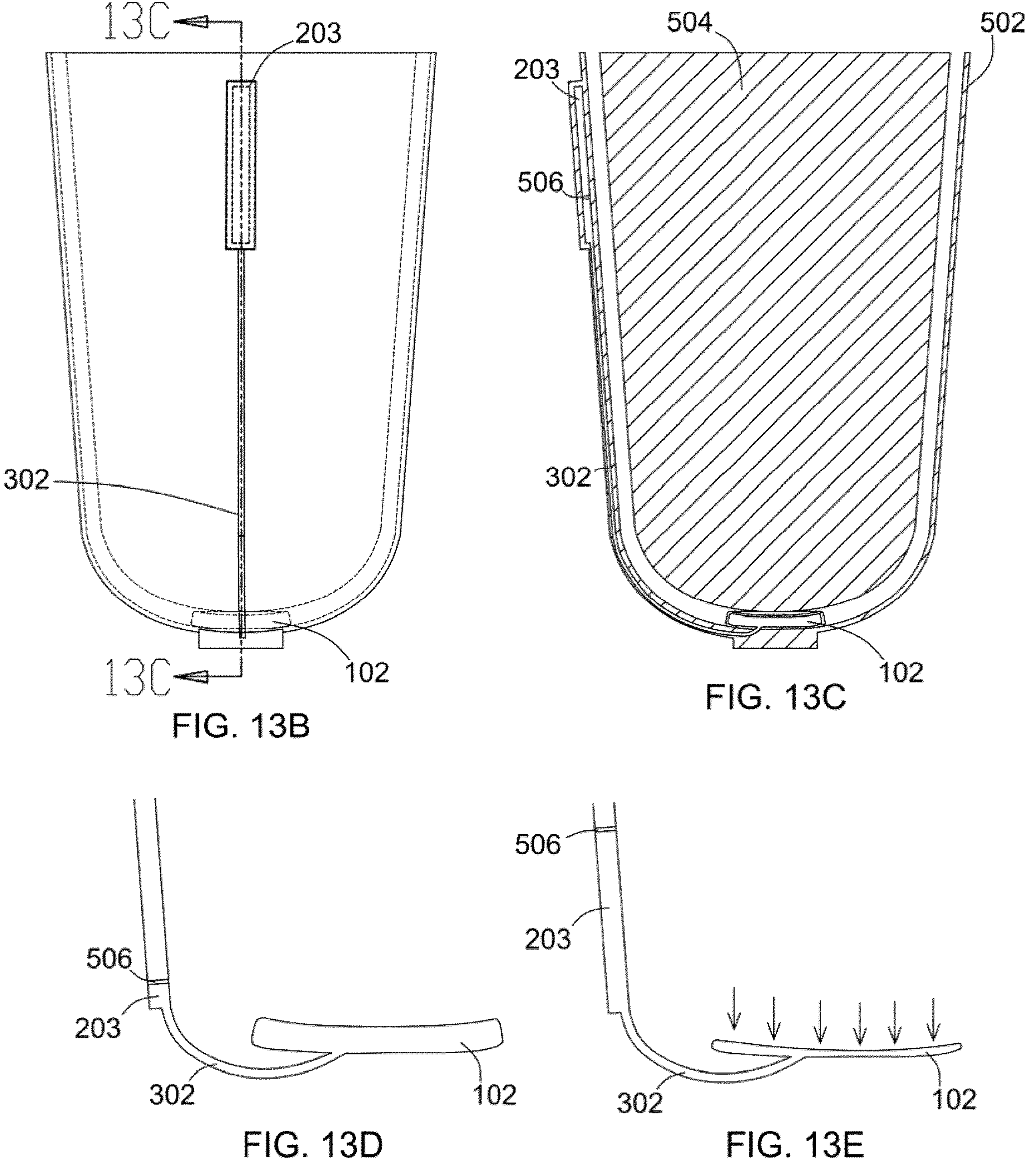
FIG. 13B is a side view showing an embodiment where the closed-loop fluidic regenerative system is used to enable fluidic sensors to detect socket fit for prostheses, as seen in FIG. 13A.
FIG. 13C is a sectional view showing an embodiment where the closed-loop fluidic regenerative system is used to enable fluidic sensors to detect socket fit for prostheses, as seen in FIG. 13B.
FIG. 13D shows the fluidic sensor and fluidic regenerative chamber when a residual limb (not shown) is not pressing on the fluidic regenerative chamber of the embodiment shown in FIG. 13A.
FIG. 13E shows the fluidic sensor and fluidic regenerative chamber when a residual limb (not shown) is partially or fully pressing on the fluidic regenerative chamber of the embodiment shown in FIG. 13A.

FIG. 11A to FIG. 11D shows another embodiment where an active compression sleeve 406 is combined with a plurality of fluidic actuators 202 that are actuated by the CLFR module. Please note that the FRC and other CLFR module sub-components may not be shown in the figures for clarity. The fluidic actuators are connected to one end of a compression band 408 as seen in FIG. 11A and FIG. 11B, when a fluidic actuator 202 may linearly expand in the direction of the smaller arrow when inflated/pressurized by fluid from at least one FRC, which would tighten the compression band 408 in the direction shown by the larger arrows, which in turn compresses a particular anatomical body part 416. Multiple fluidic actuators 202 may be connected to a single compression band 408. The compression band 408 may be elastic, flexible, and/or any combination thereof. A rigid, flexible, and/or elastic spine 412 may help guide the compression bands to tighten and relax. Fluidic conduits 302 may fluidly connect fluidic actuators 202 to fluidic distribution mechanism 306, connecting to one or a plurality of FRCs. Due to the usage of compression bands 408 which are much thinner and less insulative than traditional pneumatic bladder-type compression sleeves, cooling and/or ice pack 410 may be applied to the outside of the active compression sleeve 406 for achieving both active compression and cooling/icing simultaneously. The cooling and/or ice pack 410 may be chemically activated (i.e. endothermic reactions), electrically activated (i.e., A Peltier element), and/or purely passive (a pre-cooled material absorbing heat through conduction). Another advantage of using compression bands 408 over the traditional pneumatic bladder is that they can contour over an articulating joint 413 such as the wrist, elbow, armpit, ankle and wrist, as seen in FIG. 11C. Yet another advantage of using compression band 408 is that they may overlap each other, avoiding gaps between compression points on an anatomical body part 416, as seen in FIG. 11C. FIG. 11D is a schematic diagram showing how a plurality of FRCs 102 may sequentially activate a plurality of fluidic actuators 202 to produce sequential gradient compression. Each rectangle with slightly curved vertical edges represents at least one FRC 102. Each circle or oval represents at least one fluidic actuator 202. The line connecting the rectangle with slightly curved vertical edges and the circle or oval represents at least one fluidic pathway, including but not limited to fluidic conduit 302, fluidic distribution mechanism 306 and/or any combination thereof. The size of the rectangle with slightly curved vertical edges, circles and ovals represents the relative fluidic pressure, mass, and/or volume within at least one FRC 102 and/or fluidic actuator 202. For instance, a bigger circle may represent at least one fluidic actuator 202 with higher fluidic pressure, mass, and/or volume, and a smaller oval may represent at least one fluidic actuator 202 with a smaller fluidic pressure, mass and/or volume when compared to a bigger circle and/or oval. The same concept applies to the rectangle with slightly curved vertical edges representing FRCs 102. For instance, a smaller rectangle with slightly curved vertical edges may represent at least one FRC 102 that has given more fluidic volume, mass, and/or pressure to a fluidic actuator 202 than a larger rectangle with slightly curved vertical edges. The arrows pointing down toward the rectangle with slightly curved edges may represent the forces and/or amount of compression applied to at least one FRC 102. The size of the arrow may represent the relative amount of force and/or compression applied to at least one FRC 102. For instance, a larger arrow may represent more forces and/or compression applied to at least one FRC 102 than a smaller arrow. The vertical line on the right with solid arrowheads may represent the progression of gait, jogging, running, and/or any combination thereof from heel strike (1$^{st}$ row) at the beginning of the stance phase to the swing phase (7$^{th}$ row). The leftmost FRC 102*a* closest to the posterior side of the foot may transfer its fluidic volume, mass, and/or pressure to its corresponding fluidic actuator 202*a* first and the highest amount during heel strike followed by FRC 102*b*, then FRC 102*c*, and lastly FRC 102*d* closest at the anterior side of the foot. The amount of fluidic volume, mass, and/or pressure given to fluidic actuators may be in decreasing order from 202*a*, then 202*b*, then 202*c*, and lastly, 202*d*. The more fluidic volume, mass, and/or pressure given to the fluidic actuator, the tighter the compression bands attached to the corresponding fluidic actuator. As the stance phase progresses, shown by the 2$^{nd}$ row and then the 3$^{rd}$ row of FRC and fluidic actuators from the top of the page, the FRCs close to the anterior side are increasing squeezed/compressed resulting in more pressurization/inflation of their corresponding fluidic actuator which in turn may increase the tightness of the connected compression bands. As the foot progress through the stance phase towards toes-off, the 4$^{th}$ to the 6$^{th}$ rows shows the posterior FRCs are being decreasingly squeezed/compressed, which may result in a depressurization/deflation of their corresponding fluidic actuators, which in turn may decrease the tightness of the connected compression bands. As the foot moves into the swing phase, the 7$^{th}$ row shows that all the FRCs may return to their initial neutral condition of not being or minimally being squeezed/compressed, and their corresponding fluidic actuators also return to the initial neutral condition of their baseline pressure. The swing phase will transition to the stance phase again, and the 7$^{th}$ row goes back to the 1$^{st}$ row, and the whole cycle repeats itself continuously.

FIG. 12A to FIG. 12C shows yet another embodiment where an active compression sleeve 406 with one or a plurality of compression bands 408 may be connected to one or a plurality of fluidic actuators 202. Tubing and additional components are not shown for clarity. When pressurized, at least one fluidic actuator 202 may pull on at least one compression band 408, tightening it and exerting compression onto an anatomical part of the human body 416. In the case of a single compression band 408 connecting to a plurality of fluidic actuators 202, two connecting plates 414 may connect at least one fluidic actuator 202 to the single compression band 408, one on each side. The purpose of the connecting plate 414 is to allow uniform tension to be applied to the compression band 408 that connects to the connecting plate 414. In other words, when at least one fluidic actuator 202 pulls on the connecting plate 414, the connecting plate 414 pulls on the part of the compression band 408 it connects to. At least two connecting plates 414 may be sufficient to secure at least one fluidic actuator 202 to two edges of the compression band 408. A single fluidic actuator 202 may loop through at least one connecting plate 414 multiple times in the form of a serpentine or zig-zag pattern (FIG. 12B). In certain embodiments of the invention described herein, fluidic actuator 202 may connect directly to the compression band without first connecting to a connecting plate 414 (FIG. 12C). Due to the usage of compression bands 408 which are much thinner and less insulated than traditional pneumatic bladder-type compression sleeves, cooling and/or ice pack 410 may be applied to the outside of the active compression sleeve 406 for achieving both active compression and cooling/icing simultaneously. One potential advantage of having a single compression band 408 is that it provides inherently smooth compression without gaps. Compression band 408 may be made up of any material and/or composite materials. Different sections of a single compression band 408 may have different material properties. Compression band 408 may be elastic, flexible, compliant, soft, hard, malleable, ductile, rigid, and/or any combination thereof. Another potential advantage of having a single compression band 408 is the fact that articulating joint 412 can be easily built in by simply making the part that requires articulation more elastic and/or softer than other parts. A single compression band 408 may still be able to achieve sequential and/or gradient compression as each fluidic actuator 202 becomes pressurized one by one, thereby pulling on each corresponding pair of connecting plate 414 one by one, which in turn tightens each corresponding section and/or region of the compression band 408 in a sequence as shown by the arrows in FIG. 12A. The compression band 408 gaps underneath a fluidic actuator 202 and/or between two connecting plates 414 may be negated by having the compression band 408 overlap and/or connecting to itself at various locations with potential compression band offshoots connecting to various locations on at least one fluidic actuator 202 and/or connecting plate 414. Cinch™, Velcro™ and/or any strapping mechanism may also be employed to enable the compression band 408 to enclose and/or wrap around partially and/or the entirety of an anatomical portion of the human body 416 with and/or without gaps.

v. CLFR System With Fluidic Sensor

FIG. 13A to FIG. 13E show another embodiment where fluidic sensors 203 are actuated by the CLFR module 100 instead of fluidic actuators 202. This embodiment may be used on prosthetics 500 for prosthetic socket fit applications where the movement of residual limb within prosthetic sockets 502 (i.e., pistoning and/or distal-end sinking of the residual limb 504 within prosthetic socket 502) may be detected. Movement of residual limb within prosthetic sockets 502 may lead to skin breakdown and potentially pressure ulcers. The advantage here is that the sensing system enabled is purely mechanical without the need for batteries and/or electromechanical components, thus, making it robust, low-cost, simple to maintain, and easier to use. At least one fluidic regeneration chamber (FRC) 102 may be placed between the residual limb and the socket 502 with or without any liners and/or socks worn over the residual limb. Any materials may exist between at least one FRC 102, the residual limb, and/or the socket 502. When pistoning and/or sinking of the residual limb 504 occur within the prosthetic socket 502, at least one FRC 102 may be compressed/squeezed, as represented by the arrows seen in FIG. 13E, thereby displacing fluid within FRC 102 to move to at least one fluidic sensor 203. At least one level indicator 506 within fluidic sensors 203 may change location and/or its indication under fluidic pressure. The change of indication from the fluidic sensor 203 may be visually, audibly, and/or tactilely presented to the user. For instance, the fluidic sensor 203 may have transparent walls, and the user can visually identify the level, location, orientation and/or color of the indicator 506. Alternatively, at least one fluidic sensor 203 may produce an audible sound that may be detected by the user. Alternatively, the fluidic sensor 203 may produce a sensation in the form of vibration and/or compression that can be felt by the user. Any indication method may be combined. Any number of level indicators 506 may exist within one or a plurality of fluidic sensors 203. Any level indicator 506 may be completely dynamic where it changes position, colour, orientation indication, and/or any combination thereof according to the current/instantaneous fluidic pressure within the fluidic sensor 203. Any level indicator 506 may also be partially dynamic, where it changes position, colour, orientation, indication, and/or any combination thereof according to the maximum fluidic pressure experienced within the fluidic sensor 203. Any level indicator 506 may be reset to its initial state manually, semi-manually, and/or automatically. The fluidic sensor 203 may be elastic, flexible, rigid, and/or any combination thereof. The fluidic sensor 203 may be placed anywhere on the prosthetic socket 502. The fluidic sensor 203 may be fully integrated with, detachable, and/or separated from the prosthetic socket 502. Other components and/or modules mentioned in any embodiments of the present invention may also exist in this embodiment. The fluidic sensor may be a fluidic pressure gauge or dial.

Certain embodiments of the fluidic sensor 203, which may be elastic, flexible and/or rigid, may also be placed in between the residual limb 504 and/or any liners and/or socks worn over the residual limb and the socket 502 so that when the fluidic sensor 203 is pressurized, it may apply compression onto the residual limb 504 to improve socket fit and/or provide a therapeutic effect. Therefore, at least one fluidic sensor 203 also acts as at least one fluidic actuator simultaneously.

Similar to the knee brace embodiments of the present invention, The FRC 102 may be placed within and/or in-between weight-bearing structure of the prosthesis so that when at least one FRC 102 is compressed and/or squeezed during the stance phase of gait, at least one fluidic actuator 202 may be pressurized and/or inflated to provide compression to the residual limb to improve socket fit and/or provide therapeutic effects.

Any embodiments described herein may be purely mechanical. However, electromechanical and/or battery-powered systems and/or modules may be added. It must be noted that certain embodiments may have all of the elements described here, whereas certain other embodiments may have only part of the elements described herein. A person skilled in the art can faithfully reproduce any of the embodiments described herein.

The subject-matter disclosed herein is contemplated for use in association with Closed-Loop Fluidic Regenerative System and Active Compression Band, Apparel, Device, Footwear and Method to afford increased advantageous utilities in association with same. The subject-matter, however, is not so limited and can be readily used with other items to afford various advantageous utilities. Other embodiments may be provided.

The following represent non-limited embodiments of the subject-matter disclosed herein.

Embodiment 1. A wearable assistive device comprising: a fluidic transducers module comprising at least one fluidic transducer, wherein the fluidic transducers module is operable to receive a fluid under pressure and in response to operate the at least one fluidic transducer; a fluidic regeneration module operable to receive and to pressurize the fluid responsive to mechanical interaction with the fluidic regeneration module; and a fluidic transportation module coupled to transport the fluid between the fluidic transducers module and the fluidic regeneration module; wherein: the fluidic regeneration module comprises at least one fluidic regeneration chamber to contain the fluid, wherein the at least one fluidic regeneration chamber is mechanically compressible to pressurize the fluid in the at least one fluidic regeneration chamber to transport the fluid under pressure to the fluidic transducers module via the fluidic transportation module; and the wearable assistive device further comprises an energy return mechanism operable to return the fluid from the fluidic transducers module to the fluidic regeneration module via the fluidic transportation module when the at least one fluidic regeneration chamber is decompressed.

Embodiment 2. The wearable assistive device of Embodiment 1, wherein: the fluidic transducers module, and fluidic regeneration module, and the fluidic transportation module form a closed loop; and during use of the wearable assistive device, none of the fluid enters the wearable assistive device, and none of the fluid exits the wearable assistive device.

Embodiment 3. The wearable assistive device of Embodiment 1 or 2, wherein: the at least one fluidic regeneration chamber: comprises an elastic wall defining an interior volume of the at least one fluidic regeneration chamber; is compressible to decrease the interior volume, thereby to pressurize the fluid to transport the fluid under pressure to the fluidic transducers module via the fluidic transportation module; and is operable to rebound to increase the interior volume of the at least one fluidic regeneration chamber when the at least one fluidic regeneration chamber is decompressed, thereby to return the fluid from the fluidic transducers module to the fluidic regeneration module via the fluidic transportation module.

Embodiment 4. The wearable assistive device of Embodiment 3, wherein: the at least one fluidic regeneration chamber further comprises a spring device operable to rebound the at least one fluidic regeneration chamber.

Embodiment 5. The wearable assistive device of Embodiment 4, wherein: the spring device is positioned within the at least one fluidic regeneration chamber and operable to press against an interior surface of the wall to rebound the at least one fluidic regeneration chamber.

Embodiment 6. The wearable assistance device of any one of Embodiment 1 to 5, further comprising: a wearable equipment, wherein the at least one fluidic regeneration chamber is positioned in or on the wearable equipment for alternating compression and decompression of the at least one fluidic regeneration chamber by motion of a wearer of the wearable equipment.

Embodiment 7. The wearable assistive device of Embodiment 6, wherein: the wearable equipment comprises a footwear, and the at least one fluidic regeneration chamber is positioned in or on the footwear for alternating compression and decompression by a body weight of the wearer.

Embodiment 8. The wearable assistive device of Embodiment 7, wherein: the at least one fluidic regeneration chamber is positioned in or on a housing of the footwear.

Embodiment 9. The wearable assistive device of Embodiment 8, wherein: the housing is a cushion, an insole, a midsole, an outer sole, an orthotic, or any combination thereof.

Embodiment 10. The wearable assistive device of any one of Embodiments 7 to 9, wherein: the at least one fluidic regeneration chamber is on or in or shaped as a wedge-style foot orthotic.

Embodiment 11. The wearable assistive device of any one of Embodiments 7 to 10, wherein: the at least one fluidic transducer comprises at least one fluidic actuator operable to apply force at at least one anatomical part of a body of the wearer.

Embodiment 12. The wearable assistive device of Embodiment 11 comprising: an active knee brace comprising: at least one articulation joint; and at least one strap coupled to the articulation joint, and sized and shaped to encompass a leg of the wearer proximal a knee of the wearer; wherein: the articulation joint and the at least one strap are respectively positioned whereby the articulation joint is positionable at or adjacent the knee of the wearer when the active knee brace is worn by the wearer; the at least one fluidic actuator is positionable and operable to tighten the active knee brace about the knee of the wearer to reduce knee abduction/adduction moment when the at least one fluidic regeneration chamber is compressed.

Embodiment 13. The wearable assistive device of Embodiment 12, wherein: the at least one fluidic actuator is positioned at or proximal an inner surface of the articulation joint, and positionable between the articulation joint and the knee of the wearer when the active knee brace is worn by the wearer; and when the at least one fluidic regeneration chamber is compressed, the at least one fluidic actuator is operable to move the articulation joint away from the knee and relative to the at least one strap to tighten the active knee brace about the knee of the wearer.

Embodiment 14. The wearable assistive device of Embodiment 12, wherein: the at least one fluidic actuator is positioned on or in the at least one strap and is operable to contract the at least one strap when the at least one fluidic regeneration chamber is compressed to tighten the active knee brace about the knee of the wearer.

Embodiment 15. The wearable assistive device of Embodiments 12 to 14, wherein: when the at least one fluidic regeneration chamber is decompressed, the active knee brace is operable to squeeze or stretch the at least one fluidic actuator to return the fluid from the at least one fluidic actuator to the at least one fluidic regeneration chamber and to untighten the active knee brace about the knee of the wearer.

Embodiment 16. The wearable assistive device of Embodiments 7 to 15, wherein: the at least one fluidic regeneration chamber is positioned in or on the footwear to compress the at least one fluidic regeneration chamber during a heel-strike and stance phase of a gait of the wearer, and to decompress the at least one fluidic regeneration chamber during a swing phase of the gait of the wearer.

Embodiment 17. The wearable assistive device of Embodiment 11, further comprising: an active compression sleeve comprising at least one compression band; wherein: the at least one compression band is coupled for activation by the at least one fluidic actuator to tighten the at least one compression band around the at least one anatomical part when the at least one fluidic regeneration chamber is compressed and to untighten the at least one compression band when the at least one fluidic regeneration chamber is decompressed.

Embodiment 18. The wearable assistive device of Embodiment 17, wherein: the at least one fluidic regeneration chamber is positioned for compression during a stance phase of the gait of the wearer, and for decompression during a swing phase of a gait of the wearer.

Embodiment 19. The wearable assistive device of Embodiment 17 or 18, wherein: the at least one fluidic regeneration chamber comprises a plurality of fluidic regeneration chambers arranged from a medial of the footwear to a lateral of the footwear.

Embodiment 20. The wearable assistive device of Embodiment 17 or 18, wherein: the plurality of fluidic regeneration chambers are arranged from a posterior of the footwear to an anterior of the footwear so as to respectively compress the plurality of fluidic regeneration chambers in sequence from a heel strike to a toe lift of the stance phase of the gait of the wearer and to decompress the plurality of fluidic regeneration chambers during the swing phase of the gait of the wearer.

Embodiment 21. The wearable assistive device of Embodiment 20, wherein: the at least one fluidic actuator comprises a plurality of fluidic actuators; each one of the plurality of fluidic actuators is coupled for activation by a respectively corresponding one of the plurality of fluidic regeneration chambers; the active compression sleeve comprises a plurality of compression bands; and each one of the compression bands is coupled for activation by a respectively corresponding one of the plurality of fluidic actuators to tighten the compression band around the at least one anatomical part when the corresponding fluidic regeneration chamber is compressed and to untighten the compression band when the corresponding fluidic regeneration chamber is decompressed.

Embodiment 22. The wearable assistive device of any one of Embodiments 17 to 21 wherein: the active compression sleeve forms a gap between opposing edges, and further comprises at least one pair of connecting plates respectively positioned in opposition at the opposing edges and respectively joining opposite ends of corresponding ones of the plurality of compression bands; at least one pair of connecting plates is bridged by and coupled to opposite ends of a corresponding one of the fluidic actuators; and the corresponding one of the fluidic actuators is operable to contract to move together the at least one pair of connecting plates to draw the opposing edges of the active compression sleeve together thereby to constrict the corresponding compression bands.

Embodiment 23. The wearable assistive device of Embodiment 22, wherein: at least one of the fluidic actuators is coupled to and bridges multiple pairs of the connecting plates in a serpentine or zigzag arrangement; and the at least one of the fluidic actuators is operable to contract to move together the multiple pairs of the connecting plates thereby to constrict the corresponding compression bands.

Embodiment 24. The wearable assistive device of any one of Embodiments 7 to 10, wherein: the wearable equipment comprises a prosthesis, and the at least one fluidic regeneration chamber is positioned in or on a prosthetic socket of the prosthesis for alternating compression and decompression by a residual limb of the wearer of the prosthesis during a motion of the wearer.

Embodiment 25. The wearable assistive device of Embodiment 24, wherein the motion of the wearer comprises relative motion between the residual limb and the prosthetic socket.

Embodiment 26. The wearable assistive device of Embodiment 25, wherein: the prosthetics comprises a prosthetic leg comprising a prosthetic foot coupled with the prosthetic socket; the residual limb is a residual leg of the wearer; the at least one fluidic regeneration chamber is positioned in or on the prosthetic socket at an end of the prosthetic socket proximal the prosthetic foot; and the motion of the wearer comprises relative motion between the residual leg and the prosthetic socket during a gait of the wearer.

Embodiment 27. The wearable assistive device of Embodiment 25 or 26, wherein: the at least one fluidic transducer comprises at least one fluidic sensor operable to indicate the relative motion between the residual limb and the prosthetic socket responsive to the alternating compression and decompression of the at least one fluidic regeneration chamber.

Embodiment 28. The wearable assistive device of Embodiment 27, wherein: the at least one fluidic sensor comprises a level indicator comprising a transparent wall enabling visual identification of a level of the fluid in the level indicator.

Embodiment 29. The wearable assistive device of Embodiment 27 or 28, wherein: the at least one fluidic sensor is operable to generate an audible sound responsive to the compression of the at least one fluidic regeneration chamber.

Embodiment 30. The wearable assistive device of any one of Embodiments 27 to 29, wherein: the at least one fluidic sensor is operable to vibration and positioned to be felt by the wearer responsive to the compression of the at least one fluidic regeneration chamber.

Embodiment 31. The wearable assistive device of any one of Embodiments 1 to 30, wherein: each one of the at least one fluidic actuator is independently a Mckibben-type artificial muscle actuator, a soft fluidic actuator, a balloon actuator, a linear pneumatic piston actuator, or any combination thereof.

Embodiment 32. The wearable assistive device of any one of Embodiments 1 to 31, wherein: the fluidic transportation module comprises at least one fluidic conduit coupled for communicating the fluid between the at least one fluidic transducer and the at least one fluidic regeneration chamber.

Embodiment 33. The wearable assistive device of Embodiment 32, wherein: the fluidic transportation module further comprises at least one valve for controlling flow of the fluid between the at least one fluidic transducer and the at least one fluidic regeneration chamber.

Embodiment 34. The wearable assistive device of any one of Embodiments 1 to 33, further comprising: at least one fluid intake mechanism fluidically coupled with the fluidic transportation module for injection of the fluid into the fluidic transportation module.

Embodiment 35. The wearable assistive device of Embodiment 34, wherein: the at least one fluid intake mechanism comprises a one-way flow valve configured to couple temporarily with a syringe or fluid pumping mechanism for the injection of the fluid into the fluidic transportation module.

Embodiment 36. The wearable assistive device of Embodiment 34 or 35, wherein: the at least one fluid intake mechanism comprises a filter operable to filter the fluid when injected into the fluidic transportation module.

So that the present disclosure may be more readily understood, certain terms are defined. Unless defined otherwise, all technical and scientific terms used herein have the same meaning as commonly understood by one of ordinary skill in the art to which embodiments pertain. While many methods and materials similar, modified, or equivalent to those described herein can be used in the practice of the embodiments of the present invention without undue experimentation, the preferred materials and methods are described herein.

All terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise.

Numeric ranges recited within the specification are inclusive of the numbers defining the range and include each integer within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6, etc., as well as individual numbers within that range, for example, 1, 2, 3, 4, 5, and 6, and decimals and fractions, for example, 1.2, 3.8, 1½, and 4¾. This applies regardless of the breadth of the range.

The terms "about" or "approximately" as used herein refer to variation in the numerical quantity that can occur, for example, through typical measuring techniques and equipment, with respect to any quantifiable variable, including, but not limited to, mass, volume, time, distance, voltage, and current. Further, given solid and liquid handling procedures used in the real world, there is certain inadvertent error and variation that is likely through differences in the manufacture, source, or purity of the ingredients used to make the compositions or carry out the methods and the like. The terms "about" and "approximately" also encompass these variations. Expressions which combine the terms "about" or "approximately" with one or more bounds of a range refer to a union of the bound modified by the term "about" or "approximately" as described above, and the range having the unmodified bound. Thus, for example, the expression "at least about X" means the union of "at least X" and "about X". Similarly, "at most about Y" means the union of "at most Y" and "about Y".

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of", or when used in the claims, "consisting of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either", "one of", "only one of", or "exactly one of". "Consisting essentially of", when used in the claims, shall have its ordinary meaning as used in the field of patent law.

Embodiments of the disclosed subject-matter are described herein using the auxiliary verb "may". When used herein, unless required otherwise by the context of usage, the auxiliary verb "may" designates an embodiment of the disclosed subject-matter which possesses the addressed object without requiring necessarily that any other embodiment of the disclosed subject-matter possesses the addressed object. Thus, a statement such as "X may include Y" indicates that the disclosed subject-matter includes embodiments where X includes Y, without requiring that all disclosed embodiments include Y, and without excluding any other embodiments which do not include Y.

While the disclosed subject-matter may be embodied in many different forms, there are described in detail herein specific embodiments. The present disclosure is an exemplification of the principles of the disclosed subject-matter and is not intended to limit the disclosed subject-matter to the particular embodiments illustrated. Furthermore, the disclosed subject-matter encompasses any possible combination of some or all of the various embodiments mentioned herein. In addition the disclosed subject-matter encompasses any possible combination that also specifically excludes any one or some of the various embodiments mentioned herein.

In the preceding description, for purposes of explanation, numerous details are set forth in order to provide a thorough understanding of the embodiments. However, it will be apparent to one skilled in the art that these specific details are not required. In particular, it will be appreciated that the various additional features shown in the drawings are generally optional unless specifically identified herein as required. The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

The invention claimed is:

1. A wearable assistive device comprising:

a fluidic transducers module comprising at least one fluidic transducer, wherein the fluidic transducers module is operable to receive a fluid under pressure and in response to operate the at least one fluidic transducer;

a fluidic regeneration module operable to receive and to pressurize the fluid responsive to mechanical interaction with the fluidic regeneration module; and a fluidic transportation module coupled to transport the fluid between the fluidic transducers module and the fluidic regeneration module;

wherein:

the fluidic regeneration module comprises at least one fluidic regeneration chamber to contain the fluid, wherein the at least one fluidic regeneration chamber is mechanically compressible to pressurize the fluid in the at least one fluidic regeneration chamber to transport the fluid under pressure to the fluidic transducers module via the fluidic transportation module; and the wearable assistive device further comprises an energy return mechanism operable to return the fluid from the fluidic transducers module to the fluidic regeneration module via the fluidic transportation module when the at least one fluidic regeneration chamber is decompressed wherein the at least one fluidic regeneration chamber comprises an elastic wall defining an interior volume of the at least one fluidic regeneration chamber is compressible to decrease the interior volume, thereby to pressurize the fluid to transport the fluid under pressure to the fluidic transducers module via the fluidic transportation module; and is operable to rebound to increase the interior volume of the at least one fluidic regeneration chamber when the at least one fluidic regeneration chamber is decompressed, thereby to return the fluid from the fluidic transducers module to the fluidic regeneration module via the fluidic transportation module .

2. The wearable assistive device of claim 1, wherein:

the fluidic transducers module, and fluidic regeneration module, and the fluidic transportation module form a closed loop; and during use of the wearable assistive device, none of the fluid enters the wearable assistive device, and none of the fluid exits the wearable assistive device.

3. The wearable assistive device of claim 1, wherein:

the at least one fluidic regeneration chamber further comprises a spring device operable to rebound the at least one fluidic regeneration chamber.

4. The wearable assistive device of claim 3, wherein:

the spring device is positioned within the at least one fluidic regeneration chamber and operable to press against an interior surface of the wall to rebound the at least one fluidic regeneration chamber.

5. The wearable assistance device of claim 1, further comprising:

a wearable equipment, wherein the at least one fluidic regeneration chamber is positioned in or on the wearable equipment for alternating compression and decompression of the at least one fluidic regeneration chamber by motion of a wearer of the wearable equipment.

6. The wearable assistive device of claim 5, wherein:

the wearable equipment comprises a footwear, and the at least one fluidic regeneration chamber is positioned in or on the footwear for alternating compression and decompression by a body weight of the wearer.

7. The wearable assistive device of claim 6, wherein:

the at least one fluidic regeneration chamber is positioned in or on a housing of the footwear.

8. The wearable assistive device of claim 7, wherein:

the housing is a cushion, an insole, a midsole, an outer sole, an orthotic, or any combination thereof.

9. The wearable assistive device of claim 6, wherein:

the at least one fluidic regeneration chamber is on or in or shaped as a wedge-style foot orthotic.

10. The wearable assistive device of claim 6, wherein:

the at least one fluidic transducer comprises at least one fluidic actuator operable to apply force at at least one anatomical part of a body of the wearer.

11. The wearable assistive device of claim 10 comprising:

an active knee brace comprising:

at least one articulation joint; and at least one strap coupled to the articulation joint, and sized and shaped to encompass a leg of the wearer proximal a knee of the wearer;

wherein:

the articulation joint and the at least one strap are respectively positioned whereby the articulation joint is positionable at or adjacent the knee of the wearer when the active knee brace is worn by the wearer;

the at least one fluidic actuator is positionable and operable to tighten the active knee brace about the knee of the wearer to reduce knee abduction/adduction moment when the at least one fluidic regeneration chamber is compressed.

12. The wearable assistive device of claim 11, wherein:

the at least one fluidic actuator is positioned at or proximal an inner surface of the articulation joint, and positionable between the articulation joint and the knee of the wearer when the active knee brace is worn by the wearer; and when the at least one fluidic regeneration chamber is compressed, the at least one fluidic actuator is operable to move the articulation joint away from the knee and relative to the at least one strap to tighten the active knee brace about the knee of the wearer.

13. The wearable assistive device of claim 11, wherein:

the at least one fluidic actuator is positioned on or in the at least one strap and is operable to contract the at least one strap when the at least one fluidic regeneration chamber is compressed to tighten the active knee brace about the knee of the wearer.

14. The wearable assistive device of claim 11, wherein:

when the at least one fluidic regeneration chamber is decompressed, the active knee brace is operable to squeeze or stretch the at least one fluidic actuator to return the fluid from the at least one fluidic actuator to the at least one fluidic regeneration chamber and to untighten the active knee brace about the knee of the wearer.

15. The wearable assistive device of claim 6, wherein:

the at least one fluidic regeneration chamber is positioned in or on the footwear to compress the at least one fluidic regeneration chamber during a heel-strike and stance phase of a gait of the wearer, and to decompress the at least one fluidic regeneration chamber during a swing phase of the gait of the wearer.

16. The wearable assistive device of claim 5, wherein:

the wearable equipment comprises a prosthesis, and the at least one fluidic regeneration chamber is positioned in or on a prosthetic socket of the prosthesis for alternating compression and decompression by a residual limb of the wearer of the prosthesis during a motion of the wearer.

17. The wearable assistive device of claim 16, wherein the motion of the wearer comprises relative motion between the residual limb and the prosthetic socket.

18. The wearable assistive device of claim 17, wherein:

the prosthetics comprises a prosthetic leg comprising a prosthetic foot coupled with the prosthetic socket;

the residual limb is a residual leg of the wearer;

the at least one fluidic regeneration chamber is positioned in or on the prosthetic socket at an end of the prosthetic socket proximal the prosthetic foot; and the motion of the wearer comprises relative motion between the residual leg and the prosthetic socket during a gait of the wearer.

19. The wearable assistive device of claim 17, wherein:

the at least one fluidic transducer comprises at least one fluidic sensor operable to indicate the relative motion between the residual limb and the prosthetic socket responsive to the alternating compression and decompression of the at least one fluidic regeneration chamber.

20. The wearable assistive device of claim 19, wherein:

the at least one fluidic sensor comprises a level indicator comprising a transparent wall enabling visual identification of a level of the fluid in the level indicator.

21. The wearable assistive device of claim 19, wherein:

the at least one fluidic sensor is operable to generate an audible sound responsive to the compression of the at least one fluidic regeneration chamber.

22. The wearable assistive device of claim 19, wherein:

the at least one fluidic sensor is operable to vibration and positioned to be felt by the wearer responsive to the compression of the at least one fluidic regeneration chamber.

23. The wearable assistive device of claim 1, wherein:

each one of the at least one fluidic actuator is independently a Mckibben-type artificial muscle actuator, a soft fluidic actuator, a balloon actuator, a linear pneumatic piston actuator, or any combination thereof.

24. The wearable assistive device of claim 1, wherein:

the fluidic transportation module comprises at least one fluidic conduit coupled for communicating the fluid between the at least one fluidic transducer and the at least one fluidic regeneration chamber.

25. The wearable assistive device of claim 24, wherein:

the fluidic transportation module further comprises at least one valve for controlling flow of the fluid between the at least one fluidic transducer and the at least one fluidic regeneration chamber.

26. The wearable assistive device of claim 1, further comprising:

at least one fluid intake mechanism fluidically coupled with the fluidic transportation module for injection of the fluid into the fluidic transportation module.

27. The wearable assistive device of claim 26, wherein:

the at least one fluid intake mechanism comprises a one-way flow valve configured to couple temporarily with a syringe or fluid pumping mechanism for the injection of the fluid into the fluidic transportation module.

28. The wearable assistive device of claim 26, wherein:

the at least one fluid intake mechanism comprises a filter operable to filter the fluid when injected into the fluidic transportation module.

* * * * *